United States Patent [19]
Kast et al.

[11] Patent Number: 6,040,274
[45] Date of Patent: *Mar. 21, 2000

[54] 2-AROYLCYCLOHEXANEDIONES, THEIR PREPARATION AND THEIR USE AS HERBICIDES OR PLANT GROWTH-REGULATING AGENTS

[75] Inventors: Jürgen Kast, Böhl-Iggelheim; Marcus Vossen, Mannheim; Wolfgang von Deyn, Neustadt; Stefan Engel, Wörrstadt; Regina Luise Hill, Speyer; Uwe Kardorff, Mannheim; Martina Otten, Ludwigshafen; Peter Plath, Frankenthal; Helmut Walter, Obrigheim; Karl-Otto Westphalen, Speyer; Ulf Misslitz, Neustadt, all of Germany

[73] Assignee: BASF Aktiengesellschaft, Ludwigshafen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/809,100

[22] PCT Filed: Sep. 19, 1995

[86] PCT No.: PCT/EP95/03685

§ 371 Date: Mar. 18, 1997

§ 102(e) Date: Mar. 18, 1997

[87] PCT Pub. No.: WO96/10561

PCT Pub. Date: Apr. 11, 1996

[30] Foreign Application Priority Data

Sep. 30, 1994 [DE] Germany ............... 44 34 987

[51] Int. Cl.⁷ .................................................. A01N 31/04
[52] U.S. Cl. .................. 504/348; 568/31; 568/29; 568/37; 568/42; 568/49; 568/331; 568/329; 504/293; 504/296; 504/310; 549/427; 549/498
[58] Field of Search ............... 504/348, 293, 504/296, 310; 568/31, 29, 37, 42, 49, 329, 331; 549/427, 498

[56] References Cited

U.S. PATENT DOCUMENTS

| | | | |
|---|---|---|---|
| 4,744,820 | 5/1988 | Keil et al. ................... | 71/103 |
| 4,909,835 | 3/1990 | Tobler ....................... | 71/103 |
| 5,026,899 | 6/1991 | Tobler ....................... | 71/103 |
| 5,132,462 | 7/1992 | Tobler ....................... | 568/31 |

FOREIGN PATENT DOCUMENTS

| | | | |
|---|---|---|---|
| 233 568 | 8/1987 | European Pat. Off. .......... | 71/103 |
| 243 313 | 10/1987 | European Pat. Off. .......... | 71/103 |
| 319 075 | 6/1989 | European Pat. Off. .......... | 71/103 |
| WO 91/01289 | 2/1991 | WIPO ........................ | 71/103 |

OTHER PUBLICATIONS

Chem. Abst. JO 3052–862, no date avail.

*Primary Examiner*—James H. Reamer
*Attorney, Agent, or Firm*—Keil & Weinkauf

[57] ABSTRACT

2- Aroylcyclohexanediones I

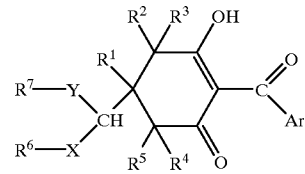

where

X, Y=O or S;

Ar=phenyl or heteroaryl in each case having 1–4 substituents: halogen, cyano, nitro, $-N=N-Ph$, $C_1-C_4$-alkoxycarbonyl, $-N(R^9)-COR^{10}$, $-N(R^9)-SO_2-R^{11}$, $-SO_2-N(R^9)R^{10}$, $-S(O)_m-R^8$ or opt. subst. $C_1-C_4$-alkyl, $C_1-C_4$-alkoxy, $C_1-C_4$-haloalkyl or $C_1-C_4$-haloalkoxy;

two adjacent C atoms of the phenyl or heteroaryl ring can also be bridged by means of a chain $-C(R^{12})=C(R^{13})-C(R^{14})=C(R^{15})-$, $-Z^1-C(R^{12})=N-$, $-Z^1-N=C(R^{12})-$, $-Z_1-C(R^{12})=C(R^{13})-$, $-Z^1-C(R^{12})=C(R^{13})-C(R^{14},R^{15})-$, $-Z^1-C(R^{12},R^{13})-C(R^{14},R^{15})-$, $-Z^1-C(R^{12},R^{13})-C(R^{14}R^{15})-Z^2-$, $-C(R^{12},R^{13})-Z^1-C(R^{14},R^{15})-C(R^{16},R^{17})-$, $-Z^1-N(R^{20})-Z^2-$, $-Z^1-Z^2-N(R^{20})-$, $-Z^1-C(R^{12},R^{13})-Z^2-N(R^{20})-$, $-Z^1-N(R^{20})-Z^2-N(R^{21})-$, $-N(R^{21})-Z^1-Z^2-$, $-N(R^{20})-Z^1-N=C(R^{12})-$, $-Z^1-C(R^{12},R^{13})-C(=NOR^{22})-$, $-Z^1-C(R^{12},R^{13})-C(R^{14},R^{15})-C(=NOR^{22})-$ or $Z^1-Z^2-Z^1$;

($Z^1$, $Z^2$=$-O-$, $-S-$, $-SO-$, $-SO_2-$, $-CO-$, $-C(R^{18},R^{19})-$ or $-N(R^{20})-$;

$R^{12}$, $R^{19}$=H, OH, halogen, $C_1-C_4$alkyl, $C_1-C_4$-alkoxy, $C_1-C_4$-alkylthio, $C_1-C_4$-alkylamino, di-($C_1-C_4$-alkyl)amino or phenyl;

$R^{20}$, $R^{21}$=H, $C_1-C_4$-alkyl, $C_1-C_4$-alkoxy, $C_1-C_4$-alkylcarbonyl, phenyl or benzoyl;

$R^{22}$=H, $C_1-C_4$-alkyl, allyl or phenyl;

Ph=phenyl, which can carry 1–3 substituents: halogen, cyano, nitro, $-S(O)_n-R^{23}$, $C_1-C_4$-alkoxycarbonyl, $-SO_2-N(R^{24})R^{25}$, $-N(R^{24})-COR^{25}$, $-N(R^{24})-SO_2R^{26}$ or opt. subst. $C_1-C_4$-alkyl, $C_1-C_4$-alkoxy, $C_1-C_4$-haloalkyl or $C_1-C_4$-haloalkoxy;

m, n=0–2;

$R^8$, $R^{23}$=opt. subst. $C_1-C_4$-alkyl or $C_1-C_4$-haloalkyl;

$R^9$,$R^{10}$,$R^{24}$,$R^{25}$=H, $C_1-C_4$-alkyl, $C_1-C_4$-haloalkyl or opt. subst. phenyl;

$R^{11}$, $R^{26}$=opt. subst. $C_1-C_4$-alkyl or $C_1-C_4$-haloalkyl)

$R^1$,$R^2$,$R^3$,$R^4$=hydrogen or $C_1-C_4$-alkyl;

$R^5$=H, $C_1-C_4$-alkyl or $C_1-C_4$-alkoxycarbonyl;

$R^6$, $R^7$ = $C_1$–$C_4$-alkyl, benzyl or together are an opt. subst. ethylene or propylene chain;

excluding 2-(4-chloro-2-nitrobenzoyl)-5-dimethoxymethyl-5-methylcyclohexane-1,3-dione, and the salts of I and esters of I with acids.

Use: herbicides; growth regulators.

12 Claims, No Drawings

2-AROYLCYCLOHEXANEDIONES, THEIR PREPARATION AND THEIR USE AS HERBICIDES OR PLANT GROWTH-REGULATING AGENTS

The present invention relates to novel 2-aroylcyclohexanediones of the formula I

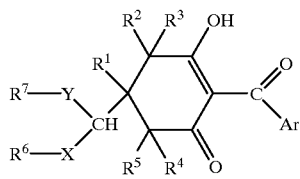

where the variables have the following meanings:

X and Y independently of one another are oxygen or sulfur;

Ar is
phenyl or a 5- or 6-membered heteroaryl ring, the phenyl or heteroaryl ring carrying at least one, but at most four substituents, in each case selected from the group consisting of halogen, cyano, nitro, —N=N—Ph, ($C_1$–$C_4$-alkoxy) carbonyl, —N($R^9$)—$COR^{10}$, —N($R^9$)—$SO_2$—$R^{11}$, —$SO_2$—N($R^9$)$R^{10}$, —S(O)$_m$—$R^8$, $C_1$–$C_4$-alkyl, $C_1$–$C_4$-alkoxy, $C_1$–$C_4$-haloalkyl and $C_1$–$C_4$-haloalkoxy, it being possible for the four last-mentioned radicals in turn to carry one or two of the following substituents: $C_1$–$C_4$-alkoxy, $C_1$–$C_4$-alkylthio and/or cyano, and it being possible for two adjacent C atoms of the phenyl or heteroaryl ring also to be bridged by means of a chain —C($R^{12}$)=C($R^{13}$)—C($R^{14}$)=C($R^{15}$)—, —$Z^1$—C($R^{12}$)=N—, —$Z^1$—N=C($R^{12}$)—, —$Z^1$—C($R^{12}$)=C($R^{13}$)—, —$Z^1$—C($R^{12}$)=C($R^{13}$)—C($R^{14}$,$R^{15}$)—, —$Z^1$—C($R^{12}$,$R^{13}$)—C($R^{14}$,$R^{15}$)—, —$Z^1$—C($R^{12}$,$R^{13}$)—C($R^{14}$,$R^{15}$)—$Z^2$—, —C($R^{12}$,$R^{13}$)—$Z_1$—C($R^{14}$,$R^{15}$)—C($R^{16}$,$R^{17}$)—, —$Z^1$—N($R^{20}$)—$Z^2$—, —$Z^1$—$Z^2$—N($R^{20}$)—, —$Z^1$—C($R^{12}$,$R^{13}$)—$Z^2$—N($R^{20}$)—, —$Z^1$—N($R^{20}$)—$Z^2$—N($R^{21}$)—, —N($R^{21}$)—$Z_1$—$Z^2$—, —N($R^{20}$)—$Z^1$—N=C($R^{12}$)—, —$Z^1$—C($R^{12}$,$R^{13}$)—C(=NOR$^{22}$)—, —$Z^1$—C($R_{12}$,$R^{13}$)—C($R_{14}$,$R^{15}$)—C(=NOR$^{22}$)— or $Z^1$—$Z^2$—$Z^1$, where $Z^1$ and $Z^2$ independently of one another are oxygen, sulfur, —SO—, —$SO_2$—, —CO—, —C($R^{18}$, $R^{19}$)— or —N($R^{20}$)— and where $R^{12}$ to $R^{19}$ independently of one another are hydrogen, halogen, hydroxyl, $C_1$–$C_4$-alkyl, $C_1$–$C_4$-alkoxy, $C_1$–$C4$-alkylthio, $C_1$–$C_4$-alkylamino, di-($C_1$–$C_4$-alkyl)amino or phenyl, $R^{20}$ and $R^{21}$ independently of one another are hydrogen, $C_1$–$C_4$-alkyl, $C_1$–$C_4$-alkoxy, ($C_1$–$C_4$-alkyl)carbonyl, phenyl or benzoyl and $R^{22}$ is
hydrogen, $C_1$–$C_4$-alkyl, allyl or phenyl;

Ph is
phenyl which can be unsubstituted or can carry one to three substituents selected from the group consisting of halogen, cyano, nitro, —S(O)$_n$—$R^{23}$, ($C_1$–$C_4$-alkoxy)carbonyl, —$SO_2$—N($R^{24}$)$R^{25}$, —N($R^{24}$)—$COR^{25}$, —N($R^{24}$)—$SO_2R^{26}$, $C_1$–$C_4$-alkyl, $C_1$–$C_4$-alkoxy, $C_1$–$C_4$-haloalkyl and $C_1$–$C_4$-haloalkoxy, it being possible for the four last-mentioned radicals in turn to carry one or two of the following substituents: $C_1$–$C_4$-alkoxy, $C_1$–$C_4$-alkylthio and/or cyano;

m and n independently of one another are 0, 1 or 2;

$R^8$ and $R^{23}$ independently of one another are $C_1$–$C_4$-alkyl or $C_1$–$C_4$-haloalkyl, which both can carry one or two $C_1$–$C_4$-alkoxy, $C_1$–$C_4$-alkylthio and/or cyano radicals;

$R^9$, $R^{10}$, $R^{24}$ and $R^{25}$ independently of one another are hydrogen, $C_1$–$C_4$-alkyl, $C_1$–$C_4$-haloalkyl or phenyl, which can be unsubstituted or can carry one to three halogen, $C_1$–$C_4$-alkyl and/or $C_1$–$C_4$-alkoxy radicals;

$R^{11}$ and $R^{26}$ independently of one another are $C_1$–$C_4$-alkyl or $C_1$–$C_4$-haloalkyl, which both can carry one or two cyano, phenyl and/or benzyl radicals;

$R^1$, $R^2$, $R^3$ and $R^4$
independently of one another are hydrogen or $C_1$–$C_4$-alkyl;

$R^5$ is
hydrogen, $C_1$–$C_4$-alkyl or ($C_1$–$C_4$-alkoxy)carbonyl;

$R^6$ and $R^7$
independently of one another are $C_1$–$C_4$-alkyl, benzyl or together are an ethylene or propylene chain, it being possible for each methylene unit to carry one or two $C_1$–$C_4$-alkyl radicals;

excluding 2-(4-chloro-2-nitrobenzoyl)-5-dimethoxymethyl-5-methylcyclohexane-1,3-dione, and the agriculturally utilizable salts of I and the esters of I with $C_1$–$C_{10}$ carboxylic, sulfonic or phosphonic acids or inorganic acids.

The invention additionally relates to processes for preparing these compounds, their use as herbicides and for regulating plant growth, and to herbicidal compositions and compositions for regulating plant growth which contain these compounds as active substances.

In addition, the invention relates to processes for preparing the herbicidal compositions and compositions for regulating plant growth, and to processes for controlling undesired plant growth and for regulating plant growth using the compounds I.

Herbicidally active 2-aroylcyclohexanediones having an ether radical in the 5-position have already been disclosed in EP-A 243 313, EP-A 319 075 and JP-A 03/052862.

2-Aroylcyclohexanediones having an acetal or thioacetal radical in the 5-position are described as herbicides, inter alia, in WO 91/01289.

According to EP-A 233 568, 5-dialkoxymethylcyclohexane-1,3-diones having an alkylcarbonyl, alkoxyalkylcarbonyl or cyclopropylcarbonyl radical in the 2-position have growth-regulating action on plants.

The herbicidal and the plant growth-regulating properties of the known compounds may only be satisfactory to a limited extent, however, particularly at low application rates and concentrations.

It is an object of the present invention to provide further 2-aroylcyclohexanediones having improved properties.

We have found that this object is achieved by the 2-aroylcyclohexanediones of the formula I defined at the beginning. We have furthermore found processes for preparing these compounds, their use as herbicides or for regulating plant growth, herbicides and plant growth-regulating compositions which contain the compounds I, processes for preparing these compositions, and processes for controlling undesired plant growth and for regulating plant growth using these compositions.

The organic entities mentioned for the substituents $R^1$ to $R^{26}$ or as radicals on phenyl rings or heterocycles, such as halogen, are collective terms for individual lists of the separate group members. All alkyl and haloalkyl moieties can be straight-chain or branched. Halogenated substituents preferably carry one to five identical or different halogen atoms.

Specific examples are:

halogen: fluorine, chlorine, bromine or iodine, preferably fluorine or chlorine;

$C_1$–$C_4$-alkyl: methyl, ethyl, n-propyl, 1-methylethyl, n-butyl, 1-methylpropyl, 2-methylpropyl or 1,1-dimethylethyl, preferably methyl or ethyl;

$C_1$–$C_4$-haloalkyl: $C_1$–$C_4$-alkyl as mentioned above, which is partially or completely substituted by fluorine, chlorine and/or bromine, eg. chloromethyl, dichloromethyl, trichloromethyl, fluoromethyl, difluoromethyl, trifluoromethyl, chlorofluoromethyl, dichlorofluoromethyl, chlorodifluoromethyl, 2-chloroethyl, 2-fluoroethyl, 2-bromoethyl, 2-iodoethyl, 2,2-difluoroethyl, 2,2,2-trifluoroethyl, 2-chloro2-fluoroethyl, 2-chloro-2,2-difluoroethyl, 2,2-dichloro-2-fluoroethyl, pentafluoroethyl, 3-fluoropropyl, 2-fluoropropyl, 2,2-difluoropropyl, 2,3-difluoropropyl, 3-chloropropyl, 2-chloropropyl, 2,3-dichloropropyl, 3-bromopropyl, 2-bromopropyl, 3,3,3-trichloropropyl, 3,3,3-trifluoropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl, preferably trifluoromethyl, difluoromethyl, 2,2,2-trifluoroethyl or pentafluoroethyl;

$C_1$–$C_4$-alkoxy: methoxy, ethoxy, n-propoxy, 1-methylethoxy, n-butoxy, 1-methylpropoxy, 2-methylpropoxy or 1,1-dimethylethoxy, preferably methoxy or ethoxy;

$C_1$–$C_4$-haloalkoxy: $C_1$–$C_4$-alkoxy as mentioned above, which is partially or completely substituted by fluorine, chlorine and/or bromine, eg. difluoromethoxy, trifluoromethoxy, chlorodifluoromethoxy, bromodifluoromethoxy, 2-fluoroethoxy, 2,2-difluoroethoxy, 2,2,2-trifluoroethoxy, 2-chloroethoxy, 2-bromoethoxy, 2-iodoethoxy, 2,2,2-trichloroetoxy, 2-chloro-2 fluoroethoxy, 2-chloro-2,2-difluoroethoxy, 2,2-dichloro-2-fluoroethoxy, 2,2,2-trichloroethoxy, pentafluoroethoxy, 3-fluoropropoxy, 2-fluoropropoxy, 2,2-difluoropropoxy, 2,3-difluoropropoxy, 3-chloropropoxy, 2-chloropropoxy, 2,3-dichloropropoxy, 3-bromopropoxy, 2-bromopropoxy, 3,3,3-trichloropropoxy, 3,3,3-trifluoropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy, preferably difluoromethoxy or trifluoromethoxy;

$C_1$–$C_4$-alkylthio: methylthio, ethylthio, n-propylthio, 1-methylethylthio, n-butylthio, 1-methylpropylthio, 2-methylpropylthio or 1,1-dimethylethylthio, preferably methylthio and ethylthio;

$C_1$–$C_4$-alkylamino: methylamino, ethylamino, n-propylamino, 1-methylethylamino, n-butylamino, 1-methylpropylamino, 2-methylpropylamino or 1,1-dimethylethylamino, preferably methylamino or ethylamino;

di-($C_1$–$C_4$-alkyl)amino: eg. N,N-dimethylamino, N,N-diethylamino, N,N-dipropylamino, N,N-di-(1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methyl-propyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino, preferably dimethylamino or diethylamino;

($C_1$–$C_4$-alkyl)carbonyl: methylcarbonyl, ethylcarbonyl, n-propylcarbonyl, 1-methylethylcarbonyl, n-butylcarbonyl, 1-methylpropylcarbonyl, 2-methylpropylcarbonyl or 1,1-dimethylethylcarbonyl, preferably methylcarbonyl;

($C_1$–$C_4$-alkoxy)carbonyl: methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl or 1,1-dimethylethoxycarbonyl, preferably methoxycarbonyl, ethoxycarbonyl or 1,1-dimethylethoxycarbonyl.

Heteroaryl is preferably a 5- or 6-membered aromatic heterocycle having one oxygen and one sulfur atom or a 5- or 6-membered aromatic heterocycle having 1 to 3 heteroatoms, selected from a group consisting of 3 nitrogen atoms and one oxygen or sulfur atom: such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl, in particular 2-pyridinyl, 3-pyridinyl and 4-pyridinyl.

The 5- or 6-membered heteroaryl rings carry at least one substituent, but at most as many as there are substitutable atoms present.

If desired, the aryl and heteroaryl rings Ar can also carry a fused 5- or 6-membered ring which can be partially unsaturated or aromatic.

With respect to the use of the 2-aroylcyclohexanediones I as herbicides or for regulating plant growth, Ar is preferably phenyl or 5- or 6-membered heteroaryl in each case having one to four, in particular one, two or three substituents, each substituent being selected from the group consisting of halogen, nitro, —N=N—Ph, —S(O)$_m$R$^8$, ($C_1$–$C_4$-alkoxy)carbonyl, —N(R$^9$)—COR$^{10}$, —N(R$^9$)—SO$_2$—R$^1$, —SO$_2$—N(R$^9$)—R$^1$, $C_1$–$C_4$-alkyl, $C_1$–$C_4$-alkoxy, $C_1$–$C_4$-haloalkyl and $C_1$–$C_4$-haloalkoxy;
or one of the following bicyclic ring systems:
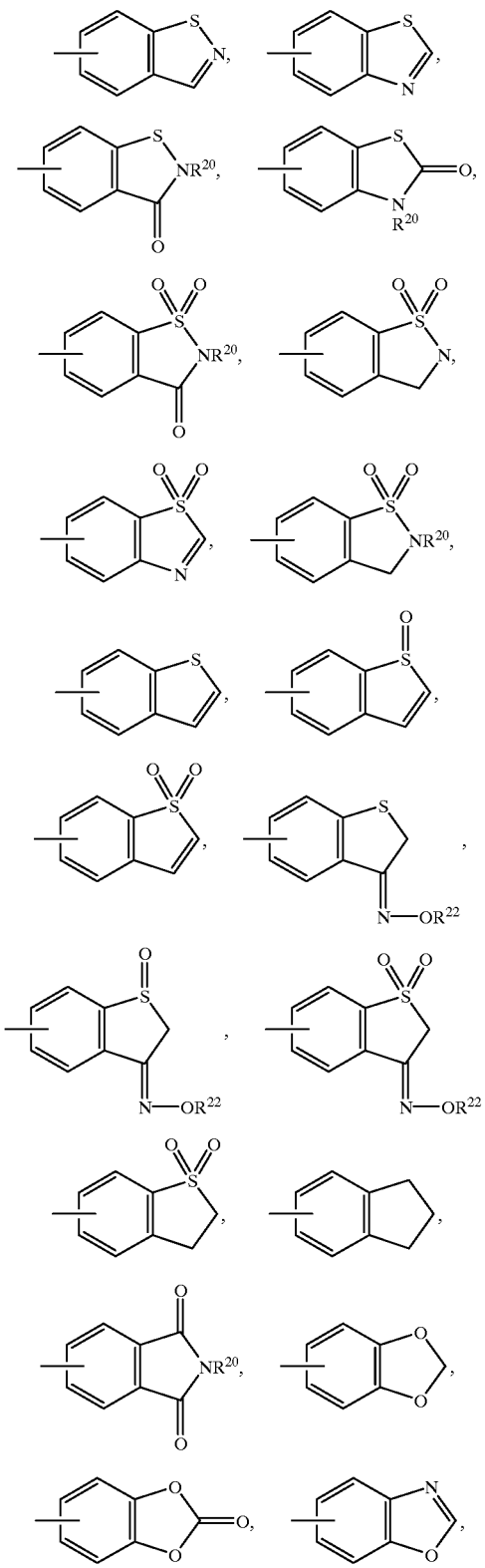
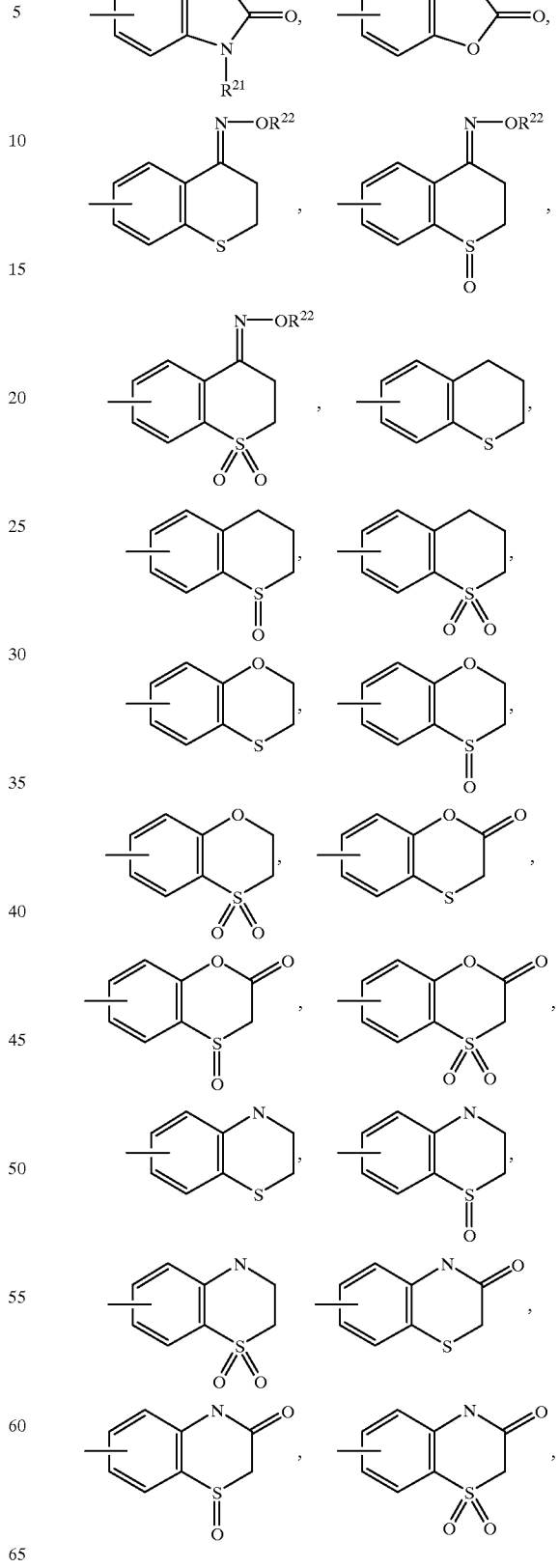

-continued

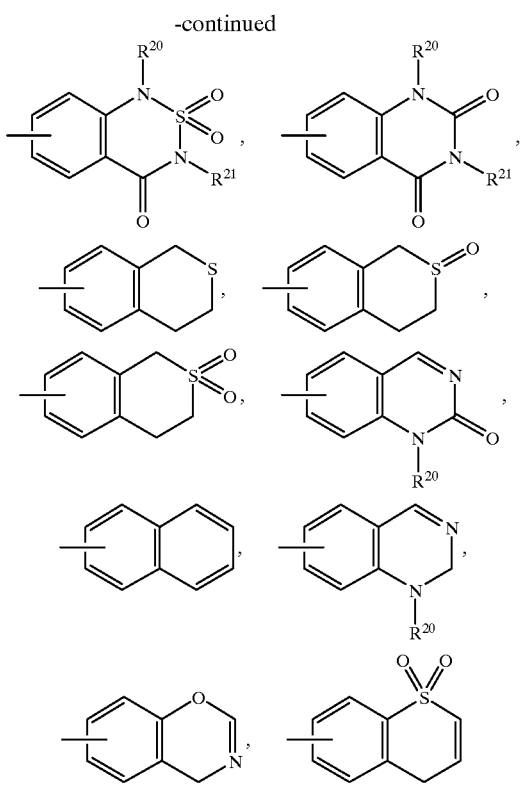

R²⁰ and R²¹ in each case preferably being hydrogen or C₁–C₄-alkyl;

Ph is preferably phenyl, which can be unsubstituted or if desired can carry one to three substituents selected from the group consisting of halogen, cyano, nitro, —S(O), —R²³, (C₁–C₄-alkoxy)-carbonyl, —SO₂—N(R²⁴)R²⁵, —N(R²⁴)—COR²⁵, —N(R²⁴)—SO₂—R²⁶C₁–C₄-alkyl, C₁–C₄-alkoxy, C₁–C₄-haloalkyl and C₁–C₄-haloalkoxy;

m and n independently of one another are 0, 1 or 2;

R⁸ and R²³ independently of one another are preferably C₁–C₄-alkyl or C₁–C₄-haloalkyl;

R⁹, R¹⁰, R²⁴ and R²⁵ independently of one another are preferably hydrogen, C₁–C₄-alkyl, phenyl or phenyl which carries one to three radicals selected from the group consisting of halogen, C₁–C₄-alkyl, C₁–C₄-haloalkyl and C₁–C₄-alkoxy;

R¹¹ and R²⁶ independently of one another are preferably C₁–C₄-alkyl or C₁–C₄-haloalkyl;

R¹ to R⁵ independently of one another are preferably hydrogen and

R⁶ and R⁷ independently of one another are preferably methyl or ethyl or together are ethylidene, propylidene or 2,2-di-(C₁–C₄-alkyl)propylidene.

Very particularly preferred compounds I are those in which at least one substituent on the phenyl or heteroaryl ring Ar is a radical —N═N—Ph, —S(O)ₘ—R⁸, (C₁–C₄-alkoxy)carbonyl, —N(R⁹)—SO₂—R¹¹, —SO₂—N(R⁹)R¹⁰, —N(R⁹)—COR¹⁰ or C₁–C₄-haloalkyl.

On account of their acidic character, the 2-aroylcyclohexanediones I according to the invention can form basic salts or enol esters, the nature of the salt or ester in general not mattering.

Customarily, suitable salts and esters are those in which the herbicidal action is not adversely affected in comparison with the free compound I.

Suitable basic salts are particularly those of the alkali metals, preferably sodium or potassium salts, the alkaline earth metals, preferably calcium and magnesium salts, those of the transition metals, preferably zinc or iron salts, as well as ammonium salts in which the ammonium ion, if desired, can carry one to three C₁–C₄-alkyl or hydroxy-C₁–C₄-alkyl substituents and/or a phenyl or benzyl substituent, preferably diisopropylammonium, tetramethylammonium, tetrabutylammonium, trimethylbenzylammonium and trimethyl-(2-hydroxyethyl)ammonium salts, and in addition phosphonium salts, sulfonium salts such as, preferably, tri-(C₁–C₄-alkyl)sulfonium salts, and sulfoxonium salts such as, preferably, tri-(C₁–C₄-alkyl)sulfoxonium salts.

Agriculturally utilizable esters are understood as meaning the esters of

C₁–C₁₀-fatty acids, in particular C₁–C₆-alkylcarboxylic acids such as methylcarboxylic acid (acetic acid), ethylcarboxylic acid (propionic acid), n-propylcarboxylic acid (butyric acid), 1-methylethylcarboxylic acid (isobutyric acid), n-butylcarboxylic acid, 1-methylpropylcarboxylic acid, 2-methylpropylcarboxylic acid, 1,1-dimethylethylcarboxylic acid, n-pentylcarboxylic acid, 1-methylbutylcarboxylic acid, 2-methylbutylcarboxylic acid, 3-methylbutylcarboxylic acid, 1,1-dimethylpropylcarboxylic acid, 1,2-dimethylpropylcarboxylic acid, 2,2-dimethylpropylcarboxylic acid, 1-ethylpropylcarboxylic acid, benzoic acid and also benzoic acids substituted by halogen, n-hexylcarboxylic acid, 1-methylpentylcarboxylic acid, 2-methylpentylcarboxylic acid, 3-methylpentylcarboxylic acid, 4-methylpentylcarboxylic acid, 1,1-dimethylbutylcarboxylic acid, 1,2-dimethylbutylcarboxylic acid, 1,3-dimethylbutylcarboxylic acid, 2,2-dimethylbutylcarboxylic acid, 2,3-dimethylbutylcarboxylic acid, 3,3-dimethylbutylcarboxylic acid, 1-ethylbutylcarboxylic acid, 2-ethylbutylcarboxylic acid, 1,1,2-trimethylpropylcarboxylic acid, 1,2,2-trimethylpropylcarboxylic acid, 1-ethyl-1-methylpropylcarboxylic acid and 1-ethyl-2-methylpropylcarboxylic acid, C₁–C₁₀-sulfonic acids, in particular C₁–C₆-alkylsulfonic acids such as methylsulfonic acid, ethylsulfonic acid, n-propylsulfonic acid, 1-methylethylsulfonic acid, n-butylsulfonic acid, 1-methylpropylsulfonic acid, 2-methylpropylsulfonic acid, 1,1-dimethylethylsulfonic acid, n-pentylsulfonic acid, 1-methylbutylsulfonic acid, 2-methylbutylsulfonic acid, 3-methylbutylsulfonic acid, 1,1-dimethylpropylsulfonic acid, 1,2-dimethylpropylsulfonic acid, 2,2-dimethylpropylsulfonic acid, 1-ethylpropylsulfonic acid, benzenesulfonic acid and benzenesulfonic acids substituted by halogen, n-hexylsulfonic acid, 1-methylpentylsulfonic acid, 2-methylpentylsulfonic acid, 3-methylpentylsulfonic acid, 4-methylpentylsulfonic acid, 1,1-dimethylbutylsulfonic acid, 1,2-dimethylbutylsulfonic acid, 1,3-dimethylbutylsulfonic acid, 2,2-dimethylbutylsulfonic acid, 2,3-dimethylbutylsulfonic acid, 3,3-dimethylbutylsulfonic acid, 1-ethylbutylsulfonic acid, 2-ethylbutylsulfonic acid, 1,1,2-trimethylpropylsulfonic acid, 1,2,2-trimethylpropylsulfonic acid, 1-ethyl-1-methylpropylsulfonic acid and 1-ethyl-2-methylpropylsulfonic acid, and $C_1$–$C_{10}$-phosphonic acids, in particular $C_1$–$C_6$-alkylphosphonic acids such as methylphosphonic acid, ethylphosphonic acid, n-propylphosphonic acid, 1-methylethylphosphonic acid, n-butylphosphonic acid, 1-methylpropylphosphonic acid, 2-methylpropylphosphonic acid, 1,1-dimethylethylphosphonic acid, n-pentylphosphonic acid, 1-methylbutylphosphonic acid, 2-methylbutylphosphonic acid, 3-methylbutylphosphonic acid, 1,1-dimethylpropylphosphonic acid, 1,2-dimethylpropylphosphonic acid, 2,2-dimethylpropylphosphonic acid, 1-ethylpropylphosphonic acid, benzenephosphonic acid and benzenephosphonic acids substituted by halogen, n-hexylphosphonic acid, 1-methylpentylphosphonic acid, 2-methylpentylphosphonic acid, 3-methylpentylphosphonic acid, 4-methylpentylphosphonic acid, 1,1-dimethylbutylphosphonic acid, 1,2-dimethylbutylphosphonic acid, 1,3-dimethylbutylphosphonic acid, 2,2-dimethylbutylphosphonic acid, 2,3-dimethylbutylphosphonic acid, 3,3-dimethylbutylphosphonic acid, 1-ethylbutylphosphonic acid, 2-ethylbutylphosphonic acid, 1,1,2-trimethylpropylphosphonic acid, 1,2,2-trimethylpropylphosphonic acid, 1-ethyl-1-methylpropylphosphonic acid and 1-ethyl-2-methylpropylphosphonic acid.

The 2-aroylcyclohexanediones I can be written in several tautomeric forms, all of which are encompassed by the invention:

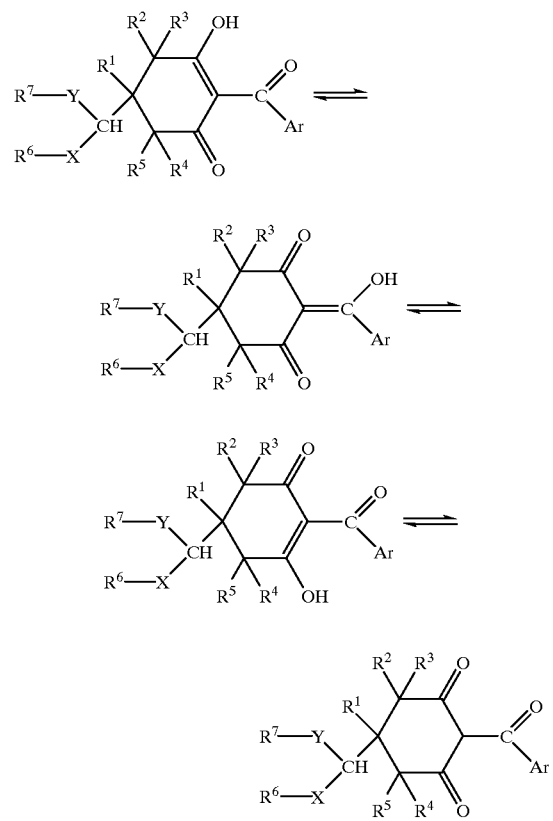

The following Table 1 lists very particularly preferred 2-aroylcyclohexanediones Ia (= I where X and Y=oxygen):

TABLE 1

Ia

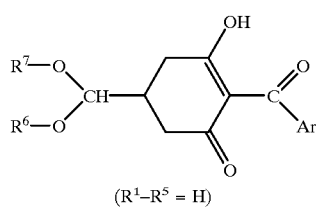

($R^1$–$R^5$ = H)

| No. | Ar | $R^6$ | $R^7$ |
|---|---|---|---|
| Ia.0010 | 2,3-$(CH_3)_2$-4-$(CH_3$—$SO_2$—)phenyl | $CH_3$ | $CH_3$ |
| Ia.0011 | 2-$(CH_3$—$SO_2$—)-4-(phenyl-N=N—)phenyl | $CH_3$ | $CH_3$ |
| Ia.0012 | 2-$(CH_3O$—)-3-$(CH_3OCH_2CH_2O$—)-4-$(CH_3SO_2$—)-phenyl | $CH_3$ | $CH_3$ |
| Ia.0013 | 2-Chloro-3-$(CH_3O$—)-4-$(CH_3SO_2$—)phenyl | $CH_3$ | $CH_3$ |
| Ia.0014 | 2-$(CH_3)$-3-$(CH_3O$—)-4-$(CH_3SO_2$—)phenyl | $CH_3$ | $CH_3$ |
| Ia.0015 | 2-Chloro-3-$(C_2H_5O$—)-4-$(C_2H_5$—$SO_2$—)phenyl | $CH_3$ | $CH_3$ |
| Ia.0016 | 2-$(CH_3)$-3-$(C_2H_5O$—)-4-$(C_2H_5$—$SO_2$—)phenyl | $CH_3$ | $CH_3$ |
| Ia.0017 | 2-Chloro-4-$(C_2H_5$—$SO_2$—)phenyl | $CH_3$ | $CH_3$ |
| Ia.0018 | 2-Nitro-4-$(C_2H_5SO_2$—)phenyl | $CH_3$ | $CH_3$ |
| Ia.0100 | 2-$(C_2H_5SO_2$—)-4-nitrophenyl | $CH_3$ | $CH_3$ |
| Ia.0101 | 2-$(C_2H_5SO_2$—)-4-chlorophenyl | $CH_3$ | $CH_3$ |
| Ia.0102 | 2,3-$(CH_3)_2$-4-$(C_2H_5SO_2)$phenyl | $CH_3$ | $CH_3$ |
| Ia.0103 | 2-Chloro-4-$(CH_3SO_2$—)phenyl | $CH_3$ | $CH_3$ |
| Ia.0104 | 4-(Phenyl-N=N—)phenyl | $CH_3$ | $CH_3$ |
| Ia.0105 | 2-$(CH_3SO_2$—)phenyl | $CH_3$ | $CH_3$ |
| Ia.0106 | 4-$(CH_3SO_2$—)phenyl | $CH_3$ | $CH_3$ |
| Ia.0107 | 2-$(CH_3SO_2$—)-4-chlorophenyl | $CH_3$ | $CH_3$ |

TABLE 1-continued

Ia $$R^7-O\diagdown CH-\diagup\diagdown-\diagup^{OH}\diagdown_{Ar}$$
$$R^6-O\diagup \diagdown \diagup\diagdown \diagdown_O$$

(R$^1$–R$^5$ = H)

| No. | Ar | R$^6$ | R$^7$ |
|---|---|---|---|
| Ia.0108 | 2-(CH$_3$SO$_2$—)-4-nitrophenyl | CH$_3$ | CH$_3$ |
| Ia.0109 | 2-Nitro-3-(CH$_3$SO$_2$—)phenyl | CH$_3$ | CH$_3$ |
| Ia.0110 | 2-Chloro-4-nitrophenyl | CH$_3$ | CH$_3$ |
| Ia.0111 | 2-Nitro-4-chlorophenyl | CH$_3$ | CH$_3$ |
| Ia.0112 | 2-Chloro-3-(CH$_3$O—CO—)-4-(CH$_3$SO$_2$—)phenyl | CH$_3$ | CH$_3$ |
| Ia.0113 | 2-(CH$_3$)-3-(CH$_3$O—CO—)-4-(CH$_3$SO$_2$—)phenyl | CH$_3$ | CH$_3$ |
| Ia.0114 | 2-(CH$_3$)-3-(CH$_3$OCH$_2$CH$_2$—)-4-(C$_2$H$_5$SO$_2$—)-phenyl | CH$_3$ | CH$_3$ |
| Ia.0115 | 2-(C$_2$H$_5$)-3-(C$_2$H$_5$O—CO—)-4-(C$_2$H$_5$SO$_2$—)-phenyl | CH$_3$ | CH$_3$ |
| Ia.0116 | 2-(C$_2$H$_5$—)-3-(CH$_3$OCH$_2$CH$_2$O—CO—)-4-(C$_2$H$_5$SO$_2$—)phenyl | CH$_3$ | CH$_3$ |
| Ia.0117 | 2-(CH$_3$—)-3-(CF$_3$O—)-4-(CH$_3$SO$_2$—)phenyl | CH$_3$ | CH$_3$ |
| Ia.0118 | 2-(CH$_3$)-3-(CH$_3$O—)-4-(CF$_3$—CH$_2$OSO$_2$—)-phenyl | CH$_3$ | CH$_3$ |
| Ia.0119 | 2-Nitro-4-[N(CH$_3$)$_2$—SO$_2$—]phenyl | CH$_3$ | CH$_3$ |
| Ia.0120 | 2-Nitro-4-(CH$_3$SO$_2$NH—)phenyl | CH$_3$ | CH$_3$ |
| Ia.0121 | 2-Chloro-4-[N(CH$_3$)$_2$—SO$_2$—]phenyl | CH$_3$ | CH$_3$ |
| Ia.0122 | 2-Chloro-4-(CH$_3$SO$_2$NH—)phenyl | CH$_3$ | CH$_3$ |
| Ia.0123 | 2-Chloro-3-(CH$_3$OCH$_2$CH$_2$O—)-4-(C$_2$H$_5$SO$_2$—)-phenyl | CH$_3$ | CH$_3$ |
| Ia.0124 | 2-Chloro-3-(C$_2$H$_5$OCH$_2$CH$_2$O—)-4-(C$_2$H$_5$SO$_2$—)-phenyl | CH$_3$ | CH$_3$ |
| Ia.0125 | 2-(CH$_3$)-3-(C$_2$H$_5$OCH$_2$CH$_2$O—)-4-(C$_2$H$_5$SO$_2$—)-phenyl | CH$_3$ | CH$_3$ |
| Ia.0126 | 2-(NCCH$_2$CH$_2$—)-3-(CH$_3$O—)-4-(CH$_3$SO$_2$—)-phenyl | CH$_3$ | CH$_3$ |
| Ia.0127 | 2-Chloro-3-(CH$_3$S—)-4-(CH$_3$SO$_2$—)phenyl | CH$_3$ | CH$_3$ |
| Ia.0128 | 2-(CH$_3$)-3-(CH$_3$S—)-4-(CH$_3$SO$_2$—)phenyl | CH$_3$ | CH$_3$ |
| Ia.0129 | 2-Bromo-3-(CH$_3$O—CO—)-4-(C$_2$H$_5$SO$_2$—)phenyl | CH$_3$ | CH$_3$ |
| Ia.0130 | 2-(CH$_3$SO$_2$—)-3-(CF$_3$O—)-4-[CH$_3$CON(CH$_3$)—]-phenyl | CH$_3$ | CH$_3$ |
| Ia.0131 | 2-Chloro-3-[(CH$_3$)$_2$CHSO$_2$—]-4-(phenyl-NHSO$_2$—)phenyl | CH$_3$ | CH$_3$ |
| Ia.0132 | 2-(CH$_3$)-3(CH$_3$SCH$_2$CH$_2$O—)-4-CH$_3$NHSO$_2$—)-phenyl | CH$_3$ | CH$_3$ |
| Ia.0133 | 2-Chloro-4-(phenyl-N=N—)phenyl | CH$_3$ | CH$_3$ |
| Ia.0134 | 2-(CH$_3$SO$_2$—)-4-cyanophenyl | CH$_3$ | CH$_3$ |
| Ia.0135 | 2-Bromo-4-(CH$_3$SO$_2$—)phenyl | CH$_3$ | CH$_3$ |
| Ia.0136 | 2-(CH$_3$SO$_2$—)-4-bromophenyl | CH$_3$ | CH$_3$ |
| Ia.0137 | 2-(CH$_3$)-3-(CH$_3$O—)-4-(NH$_2$SO$_2$—)phenyl | CH$_3$ | CH$_3$ |
| Ia.0138 | 2-(CH$_3$)-3-(CH$_3$O—)-4(CH$_3$NHSO$_2$—)phenyl | CH$_3$ | CH$_3$ |
| Ia.0139 | 2,3-Dichloro-4-(CH$_3$SO$_2$—)phenyl | CH$_3$ | CH$_3$ |
| Ia.0140 | 2-Chloro-3-(CH$_3$OCH$_2$—)-4-(CH$_3$SO$_2$—)phenyl | CH$_3$ | CH$_3$ |
| Ia.0141 | 2-Bromo-4-(phenyl-N=N—)phenyl | CH$_3$ | CH$_3$ |
| Ia.0142 | 2-Chloro-3-(CH$_3$O—)-4-(phenyl-N=N—)-phenyl | CH$_3$ | CH$_3$ |
| Ia.0143 | 2,3-(CH$_3$)$_2$-4-(CH$_3$—SO$_2$—)phenyl | C$_2$H$_5$ | C$_2$H$_5$ |
| Ia.0144 | 2-(CH$_3$—SO$_2$—)-4-(phenyl-N=N—)phenyl | C$_2$H$_5$ | C$_2$H$_5$ |
| Ia.0145 | 2-(CH$_3$O—)-3-(CH$_3$OCH$_2$CH$_2$O—)-4-(CH$_3$SO$_2$—)-phenyl | C$_2$H$_5$ | C$_2$H$_5$ |
| Ia.0146 | 2-Chloro-3-(CH$_3$O—)-4-(CH$_3$SO$_2$—)phenyl | C$_2$H$_5$ | C$_2$H$_5$ |
| Ia.0147 | 2-(CH$_3$)-3-(CH$_3$O—)-4-(CH$_3$SO$_2$—)phenyl | C$_2$H$_5$ | C$_2$H$_5$ |
| Ia.0148 | 2-Chloro-3-(C$_2$H$_5$O—)-4-(C$_2$H$_5$SO$_2$—)phenyl | C$_2$H$_5$ | C$_2$H$_5$ |
| Ia.0149 | 2-(CH$_3$)-3-(C$_2$H$_5$O—)-4-(C$_2$H$_5$SO$_2$—)phenyl | C$_2$H$_5$ | C$_2$H$_5$ |
| Ia.0150 | 2-Chloro-4-(C$_2$H$_5$SO$_2$—)phenyl | C$_2$H$_5$ | C$_2$H$_5$ |
| Ia.0151 | 2-Nitro-4-(C$_2$H$_5$SO$_2$—)phenyl | C$_2$H$_5$ | C$_2$H$_5$ |
| Ia.0152 | 2-(C$_2$H$_5$SO$_2$—)-4-nitrophenyl | C$_2$H$_5$ | C$_2$H$_5$ |
| Ia.0153 | 2-(C$_2$H$_5$SO$_2$—)-4-chlorophenyl | C$_2$H$_5$ | C$_2$H$_5$ |
| Ia.0154 | 2,3-(CH$_3$)$_2$-4-(C$_2$H$_5$SO$_2$)phenyl | C$_2$H$_5$ | C$_2$H$_5$ |
| Ia.0155 | 2-Chloro-4-(CH$_3$SO$_2$—)phenyl | C$_2$H$_5$ | C$_2$H$_5$ |
| Ia.0156 | 4-(Phenyl-N=N—)phenyl | C$_2$H$_5$ | C$_2$H$_5$ |
| Ia.0157 | 2-(CH$_3$SO$_2$—)phenyl | C$_2$H$_5$ | C$_2$H$_5$ |
| Ia.0158 | 4-(CH$_3$SO$_2$—)phenyl | C$_2$H$_5$ | C$_2$H$_5$ |
| Ia.0159 | 2-(CH$_3$SO$_2$—)-4-chlorophenyl | C$_2$H$_5$ | C$_2$H$_5$ |

TABLE 1-continued $$\text{structure Ia: cyclohexenone with OH, C(=O)Ar, ketone, and CH(OR}^6\text{)(OR}^7\text{) substituent}$$

(R$^1$–R$^5$ = H)

| No. | Ar | R$^6$ | R$^7$ |
|---|---|---|---|
| Ia.0160 | 2-(CH$_3$SO$_2$—)-4-nitrophenyl | C$_2$H$_5$ | C$_2$H$_5$ |
| Ia.0161 | 2-Nitro-4-(CH$_3$SO$_2$—)phenyl | C$_2$H$_5$ | C$_2$H$_5$ |
| Ia.0162 | 2-Chloro-4-nitrophenyl | C$_2$H$_5$ | C$_2$H$_5$ |
| Ia.0163 | 2-Nitro-4-chlorophenyl | C$_2$H$_5$ | C$_2$H$_5$ |
| Ia.0164 | 2-Chloro-3-(CH$_3$O—CO—)-4-(CH$_3$SO$_2$—)phenyl | C$_2$H$_5$ | C$_2$H$_5$ |
| Ia.0165 | 2-(CH$_3$)-3-(CH$_3$O—CO—)-4-(CH$_3$SO$_2$—)phenyl | C$_2$H$_5$ | C$_2$H$_5$ |
| Ia.0166 | 2-(CH$_3$)-3-(CH$_3$OCH$_2$CH$_2$—)-4-(C$_2$H$_5$SO$_2$—)-phenyl | C$_2$H$_5$ | C$_2$H$_5$ |
| Ia.0167 | 2-(C$_2$H$_5$)-3-(C$_2$H$_5$O—CO—)-4-(C$_2$H$_5$SO$_2$—)-phenyl | C$_2$H$_5$ | C$_2$H$_5$ |
| Ia.0168 | 2-(C$_2$H$_5$)-3-(CH$_3$OCH$_2$CH$_2$O—CO—)-4-(C$_2$H$_5$SO$_2$—)phenyl | C$_2$H$_5$ | C$_2$H$_5$ |
| Ia.0169 | 2-(CH$_3$—)-3-(CF$_3$O—)-4-(CH$_3$SO$_2$—)phenyl | C$_2$H$_5$ | C$_2$H$_5$ |
| Ia.0170 | 2-(CH$_3$)-3-(CH$_3$O—)-4-(CF$_3$—CH$_2$OSO$_2$—)phenyl | C$_2$H$_5$ | C$_2$H$_5$ |
| Ia.0171 | 2-Nitro-4-[N(CH$_3$)$_2$—SO$_2$—]phenyl | C$_2$H$_5$ | C$_2$H$_5$ |
| Ia.0172 | 2-Nitro-4-(CH$_3$SO$_2$NH—)phenyl | C$_2$H$_5$ | C$_2$H$_5$ |
| Ia.0173 | 2-Chloro-4-[N(CH$_3$)$_2$—SO$_2$—]phenyl | C$_2$H$_5$ | C$_2$H$_5$ |
| Ia.0174 | 2-Chloro-4-(CH$_3$SO$_2$NH—)phenyl | C$_2$H$_5$ | C$_2$H$_5$ |
| Ia.0175 | 2-Chloro-3-(CH$_3$OCH$_2$CH$_2$O—)-4-(C$_2$H$_5$SO$_2$—)-phenyl | C$_2$H$_5$ | C$_2$H$_5$ |
| Ia.0176 | 2-Chloro-3-(C$_2$H$_5$OCH$_2$CH$_2$O—)-4-(C$_2$H$_5$SO$_2$—)-phenyl | C$_2$H$_5$ | C$_2$H$_5$ |
| Ia.0177 | 2-(CH$_3$)-3-(C$_2$H$_5$OCH$_2$CH$_2$O—)-4-(C$_2$H$_5$SO$_2$—)-phenyl | C$_2$H$_5$ | C$_2$H$_5$ |
| Ia.0178 | 2(NCCH$_2$CH$_2$—)-3-(C$_2$H$_5$O—)-4-(CH$_3$SO$_2$—)-phenyl | C$_2$H$_5$ | C$_2$H$_5$ |
| Ia.0179 | 2-Chloro-3-(CH$_3$S—)-4-(CH$_3$SO$_2$—)phenyl | C$_2$H$_5$ | C$_2$H$_5$ |
| Ia.0180 | 2-(CH$_3$)-3-(CH$_3$S—)-4-(CH$_3$SO$_2$—)phenyl | C$_2$H$_5$ | C$_2$H$_5$ |
| Ia.0181 | 2-Bromo-3-(CH$_3$O—CO—)-4-(C$_2$H$_5$SO$_2$—)phenyl | C$_2$H$_5$ | C$_2$H$_5$ |
| Ia.0182 | 2-(CH$_3$SO$_2$—)-3-(CF$_3$O—)-4-[CH$_3$CON(CH$_3$)—]-phenyl | C$_2$H$_5$ | C$_2$H$_5$ |
| Ia.0183 | 2-Chloro-3-[(CH$_3$)$_2$CHSO$_2$—]-4-(phenyl-NHSO$_2$—)phenyl | C$_2$H$_5$ | C$_2$H$_5$ |
| Ia.0184 | 2-(CH$_3$)-3-(CH$_3$SCH$_2$CH$_2$O—)-4-(CH$_3$NHSO$_2$—)-phenyl | C$_2$H$_5$ | C$_2$H$_5$ |
| Ia.0185 | 2-Chloro-4-(phenyl-N=N—)phenyl | C$_2$H$_5$ | C$_2$H$_5$ |
| I.0186 | 2-(CH$_3$SO$_2$—)-4-cyanophenyl | C$_2$H$_5$ | C$_2$H$_5$ |
| Ia.0187 | 2-Bromo-4-(CH$_3$SO$_2$—)phenyl | C$_2$H$_5$ | C$_2$H$_5$ |
| Ia.0188 | 2-(CH$_3$SO$_2$—)-4-bromophenyl | C$_2$H$_5$ | C$_2$H$_5$ |
| Ia.0189 | 2-(CH$_3$)-3-(CH$_3$O—)-4-(NH$_2$SO$_2$—)phenyl | C$_2$H$_5$ | C$_2$H$_5$ |
| Ia.221 | 2-(CH$_3$)-3-(CH$_3$O—)-4-(CH$_3$NHSO$_2$—)phenyl | C$_2$H$_5$ | C$_2$H$_5$ |
| Ia.222 | 2,3-Dichloro-4-(CH$_3$SO$_2$—)phenyl | C$_2$H$_5$ | C$_2$H$_5$ |
| Ia.223 | 2-Chloro-3-(CH$_3$OCH$_2$—)-4-(CH$_3$SO$_2$—)phenyl | C$_2$H$_5$ | C$_2$H$_5$ |
| Ia.224 | 2-Bromo-4-(phenyl-N=N—)phenyl | C$_2$H$_5$ | C$_2$H$_5$ |
| Ia.225 | 2-Chloro-3-(CH$_3$O—)-4-(phenyl-N=N—)-phenyl | C$_2$H$_5$ | C$_2$H$_5$ |
| Ia.226 | 2-(CH$_3$SO$_2$—)-4-(phenyl-N=N—)phenyl | CH(CH$_3$)$_2$ | CH(CH$_3$)$_2$ |
| Ia.227 | 2-(CH$_3$O—)-3-(CH$_3$OCH$_2$CH$_2$O—)-4-(CH$_3$SO$_2$—)-phenyl | C(CH$_3$)$_3$ | C(CH$_3$)$_3$ |
| Ia.228 | 2-Chloro-3-(CH$_3$O—)-4-(CH$_3$SO$_2$—)phenyl | C(CH$_3$)$_3$ | C(CH$_3$)$_3$ |
| Ia.229 | 2-(CH$_3$SO$_2$—)-4-nitrophenyl | CH(CH$_3$)$_2$ | CH(CH$_3$)$_2$ |
| Ia.230 | 2-Nitro-4-(CH$_3$SO$_2$—)phenyl | CH(CH$_3$)$_2$ | CH(CH$_3$)$_2$ |
| Ia.231 | 2-Chloro-4-nitrophenyl | C(CH$_3$)$_3$ | C(CH$_3$)$_3$ |
| Ia.232 | 2-Nitro-4-chlorophenyl | C(CH$_3$)$_3$ | C(CH$_3$)$_3$ |
| Ia.233 | 2-Chloro-3-(CH$_3$O—CO—)-4-(CH$_3$SO$_2$—)phenyl | n-C$_3$H$_7$ | n-C$_3$H$_7$ |
| Ia.234 | 2-(CH$_3$)-3-(CF$_3$O—)-4-(CH$_3$SO$_2$—)phenyl | n-C$_4$H$_9$ | n-C$_4$H$_9$ |
| Ia.235 | 2-(CH$_3$)-3-(CH$_3$O—)-4-(CF$_3$—CH$_2$OSO$_2$—)phenyl | CH(CH$_3$)$_2$ | CH(CH$_3$)$_2$ |
| Ia.236 | 2-(CH$_3$)-3-(CH$_3$O—)-4-(NH$_2$SO$_2$—)phenyl | CH(CH$_3$)$_2$ | CH(CH$_3$)$_2$ |
| Ia.237 | 2-(CH$_3$)-3-(CH$_3$O—)-4-(CH$_3$NHSO$_2$—)phenyl | CH(CH$_3$)$_2$ | CH(CH$_3$)$_2$ |
| Ia.238 | 2,3-(CH$_3$)$_2$-4-(CH$_3$—SO$_2$—)phenyl | —CH$_2$—CH$_2$— | |
| Ia.239 | 2-(CH$_3$—SO$_2$—)-4-(phenyl-N=N—)phenyl | —CH$_2$—CH$_2$— | |
| Ia.240 | 2-(CH$_3$O—)-3-(CH$_3$OCH$_2$CH$_2$O—)-4-(CH$_3$SO$_2$—)-phenyl | —CH$_2$—CH$_2$— | |
| Ia.241 | 2-Chloro-3-(CH$_3$O—)-4-(CH$_3$SO$_2$—)phenyl | —CH$_2$—CH$_2$— | |
| Ia.242 | 2-(CH$_3$)-3-(CH$_3$O—)-4-(CH$_3$SO$_2$—)phenyl | —CH$_2$—CH$_2$— | |

TABLE 1-continued $$\text{Ia}$$

(R¹–R⁵ = H)

| No. | Ar | R⁶ R⁷ |
|---|---|---|
| Ia.243 | 2-Chloro-3-(C²H₅O—)-4-(C₂H₅—SO₂—)phenyl | —CH₂—CH₂— |
| Ia.244 | 2-(CH₃)-3-(C₂H₅O—)-4-(C₂H₅—SO₂—)phenyl | —CH₂—CH₂— |
| Ia.245 | 2-Chloro-4-(C₂H₅—SO₂—)phenyl | —CH₂—CH₂— |
| Ia.246 | 2-Nitro-4-(C₂H₅SO₂—)phenyl | —CH₂—CH₂— |
| Ia.247 | 2-(C₂H₅SO₂—)-4-nitrophenyl | —CH₂—CH₂— |
| Ia.248 | 2-(C₂H₅SO₂—)-4-chlorophenyl | —CH₂—CH₂— |
| Ia.249 | 2,3-(CH₃)₂-4-(C₂H₅SO₂)phenyl | —CH₂—CH₂— |
| Ia.250 | 2-Chloro-4-(CH₃SO₂—)phenyl | —CH₂—CH₂— |
| Ia.251 | 4-(Phenyl-N=N—)phenyl | —CH₂—CH₂— |
| Ia.252 | 2-(CH₃SO₂—)phenyl | —CH₂—CH₂— |
| Ia.253 | 4-(CH₃SO₂—)phenyl | —CH₂—CH₂— |
| Ia.254 | 2-(CH₃SO₂—)-4-chlorophenyl | —CH₂—CH₂— |
| Ia.255 | 2-(CH₃SO₂—)-4-nitrophenyl | —CH₂—CH₂— |
| Ia.256 | 2-Nitro-3-(CH₃SO₂—)phenyl | —CH₂—CH₂— |
| Ia.257 | 2-Chloro-4-nitrophenyl | —CH₂—CH₂— |
| Ia.258 | 2-Nitro-4-chlorophenyl | —CH₂—CH₂— |
| Ia.259 | 2-Chloro-3-(CH₃O—CO—)-4-(CH₃SO₂—)phenyl | —CH₂—CH₂— |
| Ia.260 | 2-(CH₃)-3-(CH₃O—CO—)-4-(CH₃SO₂—)phenyl | —CH₂—CH₂— |
| Ia.261 | 2-(CH₃)-3-(CH₃OCH₂CH₂—)-4-(C₂H₅SO₂—)-phenyl | —CH₂—CH₂— |
| Ia.262 | 2-(C₂H₅)-3-(C₂H₅O—CO—)-4-(C₂H₅SO₂—)phenyl | —CH₂—CH₂— |
| Ia.263 | 2-(C₂H₅—)-3-(CH₃OCH₂CH₂O—CO—)-4-(C₂H₅SO₂—)phenyl | —CH₂—CH₂— |
| Ia.264 | 2-(CH₃—)-3-(CF₃O—)-4-(CH₃SO₂—)phenyl | —CH₂—CH₂— |
| Ia.265 | 2-(CH₃)-3-(CH₃O—)-4-(CF₃—CH₂OSO₂—)phenyl | —CH₂—CH₂— |
| Ia.266 | 2-Nitro-4-[N(CH₃)₂—SO₂—]phenyl | —CH₂—CH₂— |
| Ia.267 | 2-Nitro-4-(CH₃SO₂NH—)phenyl | —CH₂—CH₂— |
| Ia.268 | 2-Chloro-4-[N(CH₃)₂—SO₂—]phenyl | —CH₂—CH₂— |
| Ia.269 | 2-Chloro-4-(CH₃SO₂NH—)phenyl | —CH₂—CH₂— |
| Ia.270 | 2-Chloro-3-(CH₃OCH₂CH₂O—)-4-(C₂H₅SO₂—)-phenyl | —CH₂—CH₂— |
| Ia.271 | 2-Chloro-3-(C₂H₅OCH₂CH₂O—)-4-(C₂H₅SO₂—)-phenyl | —CH₂—CH₂— |
| Ia.272 | 2-(CH₃)-3-(C₂H₅OCH₂CH₂O—)-4-(C₂H₅SO₂—)-phenyl | —CH₂—CH₂— |
| Ia.273 | 2-(NCCH₂CH₂—)-3-(CH₃O—)-4-(CH₃SO₂—)-phenyl | —CH₂—CH₂— |
| Ia.274 | 2-Chloro-3-(CH₃S—)-4-(CH₃SO₂—)phenyl | —CH₂—CH₂— |
| Ia.275 | 2-(CH₃)-3-3(CH₃S—)-4-(CH₃SO₂—)phenyl | —CH₂—CH₂— |
| Ia.276 | 2-Bromo-3-(CH₃O—CO—)-4-(C₂H₅SO₂—)phenyl | —CH₂—CH₂— |
| Ia.277 | 2-(CH₃SO₂—)-3-(CF₃O—)-4-[CH₃CON(CH₃)—]-phenyl | —CH₂—CH₂— |
| Ia.278 | 2-Chloro-3-[(CH₃)₂CHSO₂—]-4-(phenyl-NHSO₂—)phenyl | —CH₂—CH₂— |
| Ia.279 | 2-(CH₃)-3(CH₃SCH₂CH₂O—)-4-CH₃NHSO₂—)-phenyl | —CH₂—CH₂— |
| Ia.280 | 2-Chloro-4-(phenyl-N=N—)phenyl | —CH₂—CH₂— |
| Ia.281 | 2-(CH₃SO₂—)-4-cyanophenyl | —CH₂—CH₂— |
| Ia.282 | 2-Bromo-4-(CH₃SO₂—)phenyl | —CH₂—CH₂— |
| Ia.283 | 2-(CH₃SO₂—)-4-bromophenyl | —CH₂—CH₂— |
| Ia.284 | 2-(CH₃)-3-(CH₃O—)-4-(NH₂SO₂—)phenyl | —CH₂—CH₂— |
| Ia.285 | 2-(CH₃)-3-(CH₃O—)-4(CH₃NHSO₂—)phenyl | —CH₂—CH₂— |
| Ia.286 | 2,3-Dichloro-4-(CH₃SO₂—)phenyl | —CH₂—CH₂— |
| Ia.287 | 2-Chloro-3-(CH₃OCH₂—)-4-(CH₃SO₂—)phenyl | —CH₂—CH₂— |
| Ia.288 | 2-Bromo-4-(phenyl-N=N—)phenyl | —CH₂—CH₂— |
| Ia.289 | 2-Chloro-3-(CH₃O—)-4-(phenyl-N=N—)-phenyl | —CH₂—CH₂— |
| Ia.290 | 2,3-(CH₃)₂-4-(CH₃—SO₂—)phenyl | —CH₂—C(CH₃)₂—CH₂— |
| Ia.291 | 2-(CH₃—SO₂—)-4-(phenyl-N=N—)phenyl | —CH₂—C(CH₃)₂—CH₂— |
| Ia.292 | 2-(CH₃O—)-3-(CH₃OCH₂CH₂O—)-4-(CH₃SO₂—)-phenyl | —CH₂—C(CH₃)₂—CH₂— |
| Ia.293 | 2-Chloro-3-(CH₃O—)-4-(CH₃SO₂—)phenyl | —CH₂—C(CH₃)₂—CH₂— |
| Ia.294 | 2-(CH₃)-3-(CH₃O—)-4-(CH₃SO₂—)phenyl | —CH₂—C(CH₃)₂—CH₂— |
| Ia.295 | 2-Chloro-3-(C₂H₅O—)-4-(C₂H₅—SO₂—)phenyl | —CH₂—C(CH₃)₂—CH₂— |
| Ia.296 | 2-(CH₃)-3-(C₂H₅O—)-4-(C₂H₅—SO₂—)phenyl | —CH₂—C(CH₃)₂—CH₂— |

TABLE 1-continued $$\text{Ia}$$

(R¹–R⁵ = H)

| No. | Ar | R⁶ | R⁷ |
|---|---|---|---|
| Ia.297 | 2-Chloro-4-(C₂H₅—SO₂—)phenyl | —CH₂—C(CH₃)₂—CH₂— | |
| Ia.298 | 2-Nitro-4-(C₂H₅SO₂—)phenyl | —CH₂—C(CH₃)₂—CH₂— | |
| Ia.299 | 2-(C₂H₅SO₂—)-4-nitrophenyl | —CH₂—C(CH₃)₂—CH₂— | |
| Ia.300 | 2-(C₂H₅SO₂—)-4-chlorophenyl | —CH₂—C(CH₃)₂—CH₂— | |
| Ia.301 | 2,3-(CH₃)₂-4-(C₂H₅SO₂)phenyl | —CH₂—C(CH₃)₂—CH₂— | |
| Ia.302 | 2-Chloro-4-(CH₃SO₂—)phenyl | —CH₂—C(CH₃)₂—CH₂— | |
| Ia.303 | 4-(Phenyl-N=N—)phenyl | —CH₂—C(CH₃)₂—CH₂— | |
| Ia.304 | 2-(CH₃SO₂—)phenyl | —CH₂—C(CH₃)₂—CH₂— | |
| Ia.305 | 4-(CH₃SO₂—)phenyl | —CH₂—C(CH₃)₂—CH₂— | |
| Ia.306 | 2-(CH₃SO₂—)-4-chlorophenyl | —CH₂—C(CH₃)₂—CH₂— | |
| Ia.307 | 2-(CH₃SO₂—)-4-nitrophenyl | —CH₂—C(CH₃)₂—CH₂— | |
| Ia.308 | 2-Nitro-3-(CH₃SO₂—)phenyl | —CH₂—C(CH₃)₂—CH₂— | |
| Ia.309 | 2-Chloro-4-nitrophenyl | —CH₂—C(CH₃)₂—CH₂— | |
| Ia.310 | 2-Nitro-4-chlorophenyl | —CH₂—C(CH₃)₂—CH₂— | |
| Ia.311 | 2-Chloro-3-(CH₃O—CO—)-4-(CH₃SO₂—)phenyl | —CH₂—C(CH₃)₂—CH₂— | |
| Ia.312 | 2-(CH₃)-3-(CH₃O—CO—)-4-(CH₃SO₂—)phenyl | —CH₂—C(CH₃)₂—CH₂— | |
| Ia.313 | 2-(CH₃)-3-(CH₃OCH₂CH₂—)-4-(C₂H₅SO₂—)-phenyl | —CH₂—C(CH₃)₂—CH₂— | |
| Ia.314 | 2-(C₂H₅)-3-(C₂H₅O—CO—)-4-(C₂H₅SO₂—)phenyl | —CH₂—C(CH₃)₂—CH₂— | |
| Ia.315 | 2-(C₂H₅—)-3-(CH₃OCH₂CH₂O—CO—)-4-(C₂H₅SO₂—)phenyl | —CH₂—C(CH₃)₂—CH₂— | |
| Ia.316 | 2-(CH₃—)-3-(CF₃O—)-4-(CH₃SO₂—)phenyl | —CH₂—C(CH₃)₂—CH₂— | |
| Ia.317 | 2-(CH₃—)-3-(CH₃O—)-4-(CF₃—CH₂OSO₂—)phenyl | —CH₂—C(CH₃)₂—CH₂— | |
| Ia.318 | 2-Nitro-4-[N(CH₃)₂—SO₂—]phenyl | —CH₂—C(CH₃)₂—CH₂— | |
| Ia.319 | 2-Nitro-4-(CH₃SO₂NH—)phenyl | —CH₂—C(CH₃)₂—CH₂— | |
| Ia.320 | 2-Chloro-4-[N(CH₃)₂—SO₂—]phenyl | —CH₂—C(CH₃)₂—CH₂— | |
| Ia.321 | 2-Chloro-4-(CH₃SO₂NH—)phenyl | —CH₂—C(CH₃)₂—CH₂— | |
| Ia.322 | 2-Chloro-3-(CH₃OCH₂CH₂O—)-4-(C₂H₅SO₂—)-phenyl | —CH₂—C(CH₃)₂—CH₂— | |
| Ia.323 | 2-Chloro-3-(C₂H₅OCH₂CH₂O—)-4-(C₂H₅SO₂—)-phenyl | —CH₂—C(CH₃)₂—CH₂— | |
| Ia.324 | 2-(CH₃)-3-(C₂H₅OCH₂CH₂O—)-4-(C₂H₅SO₂—)-phenyl | —CH₂—C(CH₃)₂—CH₂— | |
| Ia.325 | 2-(NCCH₂CH₂—)-3-(CH₃O—)-4-(CH₃SO₂—)-phenyl | —CH₂—C(CH₃)₂—CH₂— | |
| Ia.326 | 2-Chloro-3-(CH₃S—)-4-(CH₃SO₂—)phenyl | —CH₂—C(CH₃)₂—CH₂— | |
| Ia.327 | 2-(CH₃)-3-(CH₃S—)-4-(CH₃SO₂—)phenyl | —CH₂—C(CH₃)₂—CH₂— | |
| Ia.328 | 2-Bromo-3-(CH₃O—CO—)-4-(C₂H₅SO₂—)phenyl | —CH₂—C(CH₃)₂—CH₂— | |
| Ia.329 | 2-(CH₃SO₂—)-3-(CF₃O—)-4-[CH₃CON(CH₃)—]-phenyl | —CH₂—C(CH₃)₂—CH₂— | |
| Ia.330 | 2-Chloro-3-[(CH₃)₂CHSO₂—]-4-(phenyl-NHSO₂—)phenyl | —CH₂—C(CH₃)₂—CH₂— | |
| Ia.331 | 2-(CH₃)-3(CH₃SCH₂CH₂O—)-4-(CH₃NHSO₂—)-phenyl | —CH₂—C(CH₃)₂—CH₂— | |
| Ia.332 | 2-Chloro-4-(phenyl-N=N—)phenyl | —CH₂—C(CH₃)₂—CH₂— | |
| Ia.333 | 2-(CH₃SO₂—)-4-cyanophenyl | —CH₂—C(CH₃)₂—CH₂— | |
| Ia.334 | 2-Bromo-4-(CH₃SO₂—)phenyl | —CH₂—C(CH₃)₂—CH₂— | |
| Ia.335 | 2-(CH₃SO₂—)-4-bromophenyl | —CH₂—C(CH₃)₂—CH₂— | |
| Ia.336 | 2-(CH₃)-3-(CH₃O—)-4-(NH₂SO₂—)phenyl | —CH₂—C(CH₃)₂—CH₂— | |
| Ia.337 | 2-(CH₃)-3-(CH₃O—)-4(CH₃NHSO₂—)phenyl | —CH₂—C(CH₃)₂—CH₂— | |
| Ia.338 | 2,3-Dichloro-4-(CH₃SO₂—)phenyl | —CH₂—C(CH₃)₂—CH₂— | |
| Ia.339 | 2-Chloro-3-(CH₃OCH₂—)-4-(CH₃SO₂—)phenyl | —CH₂—C(CH₃)₂—CH₂— | |
| Ia.340 | 2-Bromo-4-(phenyl-N=N—)phenyl | —CH₂—C(CH₃)₂—CH₂— | |
| Ia.341 | 2-Chloro-3-(CH₃O—)-4-(phenyl-N=N—)-phenyl | —CH₂—C(CH₃)₂—CH₂— | |
| Ia.342 | 2-Chloro-3-chloro-4-(CH₃O—)phenyl | —CH₃ | —CH₃ |
| Ia.343 | 2-Chloro-3-chloro-4-(CH₃SO₂—)phenyl | —CH₃ | —CH₃ |
| Ia.344 | 2-Chloro-3-chloro-4-(C₂H₅SO₂—)phenyl | —CH₃ | —CH₃ |
| Ia.345 | 2-Chloro-3-OCF₃-4-(CH₃)SO₂—)phenyl | —CH₃ | —CH₃ |
| Ia.346 | 2-Chloro-3-OCF₃-4-(C₂H₅SO₂—)phenyl | —CH₃ | —CH₃ |
| Ia.347 | 2-Chloro-3-OC₂F₅-4-(C₂H₅SO₂—)phenyl | —CH₃ | —CH₃ |
| Ia.348 | 2-Chloro-3-OC₂F₅-4-(CH₃SO₂—)phenyl | —CH₃ | —CH₃ |
| Ia.349 | 2-Chloro-3-CH₃-4-(CH₃SO₂—)phenyl | —CH₃ | —CH₃ |
| Ia.350 | 2-Chloro-3-CH₃-4-(C₂H₅SO₂—)phenyl | —CH₃ | —CH₃ |
| Ia.351 | 2-Chloro-3-chloro-4-(CH₃O—)phenyl | —C₂H₅ | —C₂H₅ |

TABLE 1-continued

Ia, structure with OH, R⁷—O—CH(—O—R⁶), C(=O)Ar, and cyclohexenedione core (R¹–R⁵ = H)

| No. | Ar | R⁶ | R⁷ |
|---|---|---|---|
| Ia.352 | 2-Chloro-3-chloro-4-($CH_3SO_2$—)phenyl | —$C_2H_5$ | —$C_2H_5$ |
| Ia.353 | 2-Chloro-3-chloro-4-($C_2H_5SO_2$—)phenyl | —$C_2H_5$ | —$C_2H_5$ |
| Ia.354 | 2-Chloro-3-$OCF_3$-4-($CH_3SO_2$—)phenyl | —$C_2H_5$ | —$C_2H_5$ |
| Ia.355 | 2-Chloro-3-$OCF_3$-4-($C_2H_5SO_2$—)phenyl | —$C_2H_5$ | —$C_2H_5$ |
| Ia.356 | 2-Chloro-3-$OC_2F_5$-4-($C_2H_5SO_2$—)phenyl | —$C_2H_5$ | —$C_2H_5$ |
| Ia.357 | 2-Chloro-3-$OC_2F_5$-4-($CH_3SO_2$—)phenyl | —$C_2H_5$ | —$C_2H_5$ |
| Ia.358 | 2-Chloro-3-$CH_3$-4-($CH_3SO_2$—)phenyl | —$C_2H_5$ | —$C_2H_5$ |
| Ia.359 | 2-Chloro-3-$CH_3$-4-($C_2H_5SO_2$—)phenyl | —$C_2H_5$ | —$C_2H_5$ |
| Ia.360 | 2-Chloro-3-chloro-4-($CH_3O$—)phenyl | —$CH_2CH_2$— | |
| Ia.361 | 2-Chloro-3-chloro-4-($CH_3SO_2$—)phenyl | —$CH_2CH_2$— | |
| Ia.362 | 2-Chloro-3-chloro-4-($C_2H_5SO_2$—)phenyl | —$CH_2CH_2$— | |
| Ia.363 | 2-Chloro-3-$OCF_3$-4-($CH_3SO_2$—)phenyl | —$CH_2CH_2$— | |
| Ia.364 | 2-Chloro-3-$OCF_3$-4-($C_2H_5SO_2$—)phenyl | —$CH_2CH_2$— | |
| Ia.365 | 2-Chloro-3-$OC_2F_5$-4-($C_2H_5SO_2$—)phenyl | —$CH_2CH_2$— | |
| Ia.366 | 2-Chloro-3-$OC_2F_5$-4-($CH_3SO_2$—)phenyl | —$CH_2CH_2$— | |
| Ia.367 | 2-Chloro-3-$CH_3$-4-($CH_3SO_2$—)phenyl | —$CH_2CH_2$— | |
| Ia.368 | 2-Chloro-3-$CH_3$-4-($C_2H_5SO_2$—)phenyl | —$CH_2CH_2$— | |
| Ia.369 | 2-Chloro-3-chloro-4-($CH_3O$—)phenyl | —$CH_2C(CH_3)_2$—$CH_2$— | |
| Ia.370 | 2-Chloro-3-chloro-4-($CH_3SO_2$—)phenyl | —$CH_2C(CH_3)_2$—$CH_2$— | |
| Ia.371 | 2-Chloro-3-chloro-4-($C_2H_5SO_2$—)phenyl | —$CH_2C(CH_3)_2$—$CH_2$— | |
| Ia.372 | 2-Chloro-3-$OCF_3$-4-($CH_3SO_2$—)phenyl | —$CH_2C(CH_3)_2$—$CH_2$— | |
| Ia.373 | 2-Chloro-3-$OCF_3$-4-($C_2H_5SO_2$—)phenyl | —$CH_2C(CH_3)_2$—$CH_2$— | |
| Ia.374 | 2-Chloro-3-$OC_2F_5$-4-($C_2H_5SO_2$—)phenyl | —$CH_2C(CH_3)_2$—$CH_2$— | |
| Ia.375 | 2-Chloro-3-$OC_2F_5$-4-($CH_3SO_2$—)phenyl | —$CH_2C(CH_3)_2$—$CH_2$— | |
| Ia.376 | 2-Chloro-3-$CH_3$-4-($CH_3SO_2$—)phenyl | —$CH_2C(CH_3)_2$—$CH_2$— | |
| Ia.377 | 2-Chloro-3-$CH_3$-4-($C_2H_5SO_2$—)phenyl | —$CH_2C(CH_3)_2$—$CH_2$— | |
| Ia.378 | 2-Chloro-3-chloro-4-($CH_3O$—)phenyl | —$CH_2CH_2CH_2$— | |
| Ia.379 | 2-Chloro-3-chloro-4-($CH_3SO_2$—)phenyl | —$CH_2CH_2CH_2$— | |
| Ia.380 | 2-Chloro-3-chloro-4-($C_2H_5SO_2$—)phenyl | —$CH_2CH_2CH_2$— | |
| Ia.381 | 2-Chloro-3-$OCF_3$-4-($CH_3SO_2$—)phenyl | —$CH_2CH_2CH_2$— | |
| Ia.382 | 2-Chloro-3-$OCF_3$-4-($C_2H_5SO_2$—)phenyl | —$CH_2CH_2CH_2$— | |
| Ia.383 | 2-Chloro-3-$OC_2F_5$-4-($C_2H_5SO_2$—)phenyl | —$CH_2CH_2CH_2$— | |
| Ia.384 | 2-Chloro-3-$OC_2F_5$-4-($CH_3SO_2$—)phenyl | —$CH_2CH_2CH_2$— | |
| Ia.385 | 2-Chloro-3-$CH_3$-4-($CH_3SO_2$—)phenyl | —$CH_2CH_2CH_2$— | |
| Ia.386 | 2-Chloro-3-$CH_3$-4-($C_2H_5SO_2$—)phenyl | —$CH_2CH_2CH_2$— | |
| Ia.387 | 2,3-($CH_3$)$_2$-4-($CH_3$—$CO_2$—)phenyl | —$CH_2CH_2CH_2$— | |
| Ia.388 | 2-($CH_3$—$SO_2$—)-4-(phenyl-N=N—)phenyl | —$CH_2CH_2CH_2$— | |
| Ia.389 | 2-($CH_3O$—)-3-($CH_3OCH_2CH_2O$)-4-($CH_3SO_2$—)-phenyl | —$CH_2CH_2CH_2$— | |
| Ia.390 | 2-Chloro-3-($CH_3O$—)-4-($CH_3SO_2$—)phenyl | —$CH_2CH_2CH_2$— | |
| Ia.391 | 2-($CH_3$)-3-($CH_3O$—)-4-($CH_3SO_2$—)phenyl | —$CH_2CH_2CH_2$— | |
| Ia.392 | 2-Chloro-3-($C_2H_5O$—)-4-($C_2H_5SO_2$—)phenyl | —$CH_2CH_2CH_2$— | |
| Ia.393 | 2-($CH_3$)-3-($C_2H_5O$—)-4-($C_2H_5SO_2$—)phenyl | —$CH_2CH_2CH_2$— | |
| Ia.394 | 2-Chloro-4-($C_2H_5SO_2$—)phenyl | —$CH_2CH_2CH_2$— | |
| Ia.395 | 2-Nitro-4-($C_2H_5SO_2$—)phenyl | —$CH_2CH_2CH_2$— | |
| Ia.396 | 2-($C_2H_5SO_2$—)-4-nitrophenyl | —$CH_2CH_2CH_2$— | |
| Ia.397 | 2-($C_2H_5SO_2$—)-4-chlorophenyl | —$CH_2CH_2CH_2$— | |
| Ia.398 | 2,3-($CH_3$)$_2$-4-($C_2H_5SO_2$)phenyl | —$CH_2CH_2CH_2$— | |
| Ia.399 | 2-Chloro-4-($CH_3SO_2$—)phenyl | —$CH_2CH_2CH_2$— | |
| Ia.400 | 4-(Phenyl-N=N—)phenyl | —$CH_2CH_2CH_2$— | |
| Ia.401 | 2-($CH_3SO_2$—)phenyl | —$CH_2CH_2CH_2$— | |
| Ia.402 | 4-($CH_3SO_2$—)phenyl | —$CH_2CH_2CH_2$— | |
| Ia.403 | 2-($CH_3SO_2$—)-4-chlorophenyl | —$CH_2CH_2CH_2$— | |
| Ia.404 | 2-($CH_3SO_2$—)-4-nitrophenyl | —$CH_2CH_2CH_2$— | |
| Ia.405 | 2-Nitro-3-($CH_3SO_2$—)phenyl | —$CH_2CH_2CH_2$— | |
| Ia.406 | 2-Chloro-4-nitrophenyl | —$CH_2CH_2CH_2$— | |
| Ia.407 | 2-Nitro-4-chlorophenyl | —$CH_2CH_2CH_2$— | |
| Ia.408 | 2-Chloro-3-($CH_3O$—CO—)-4-($CH_3SO_2$—)phenyl | —$CH_2CH_2CH_2$— | |
| Ia.409 | 2-($CH_3$)-3-($CH_3O$—CO—)-4-($CH_3SO_2$—)phenyl | —$CH_2CH_2CH_2$— | |
| Ia.410 | 2-($CH_3$)-3-($CH_3OCH_2CH_2$—)-4-($C_2H_5SO_2$—)-phenyl | —$CH_2CH_2CH_2$— | |
| Ia.411 | 2-($C_2H_5$)-3-($C_2H_5O$—CO—)-4-($C_2H_5SO_2$—)-phenyl | —$CH_2CH_2CH_2$— | |
| Ia.412 | 2-($C_2H_5$)-3-($CH_3OCH_2CH_2O$—CO—)-4-($C_2H_5SO_2$—)phenyl | —$CH_2CH_2CH_2$— | |

TABLE 1-continued

Ia

R⁷—O\
     CH—[cyclohexenone with OH, C(=O)Ar, =O]\
R⁶—O/

(R¹–R⁵ = H)

| No. | Ar | R⁶ | R⁷ |
|---|---|---|---|
| Ia.413 | 2-(CH³)-3-(CF₃O—)-4-(CH₃SO₂—)phenyl | —CH₂CH₂CH₂— | |
| Ia.414 | 2-(CH₃)-3-(CH₃O—)-4-(CF₃—CH₂OSO₂—)phenyl | —CH₂CH₂CH₂— | |
| Ia.415 | 2-Nitro-4-[N(CH₃)₂—SO₂—)phenyl | —CH₂CH₂CH₂— | |
| Ia.295 | 2-Nitro-4-(CH₃SO₂NH—)phenyl | —CH₂CH₂CH₂— | |
| Ia.296 | 2-Chloro-4-[N(CH₃)₂—SO₂—]phenyl | —CH₂CH₂CH₂— | |
| Ia.297 | 2-Chloro-4-(CH₃SO₂NH—)phenyl | —CH₂CH₂CH₂— | |
| Ia.298 | 2-Chloro-3-(CH₃OCH₂CH₂O—)-4-(C₂H₅SO₂—)-phenyl | —CH₂CH₂CH₂— | |
| Ia.299 | 2-Chloro-3-(C₂H₅OCH₂CH₂O—)-4-(C₂H₅SO₂—)-phenyl | —CH₂CH₂CH₂— | |
| Ia.300 | 2-(CH₃)-3-(C₂H₅OCH₂CH₂O—)-4-(C₂H₅SO₂—)-phenyl | —CH₂CH₂CH₂— | |
| Ia.301 | 2-(NCCH₂CH₂—)-3-(CH₃O—)-4-(CH₃SO₂—)-phenyl | —CH₂CH₂CH₂— | |
| Ia.302 | 2-Chloro-3-(CH₃S—)-4-(CH₃SO₂—)phenyl | —CH₂CH₂CH₂— | |
| Ia.303 | 2-(CH₃)-3-(CH₃S—)-4-(CH₃SO₂—)phenyl | —CH₂CH₂CH₂— | |
| Ia.304 | 2-Bromo-3-(CH₃O—CO—)-4-(C₂H₅SO₂—)phenyl | —CH₂CH₂CH₂— | |
| Ia.305 | 2-(CH₃SO₂—)-3-(CF₃O—)-4-[CH₃CON(CH₃)—]-phenyl | —CH₂CH₂CH₂— | |
| Ia.306 | 2-Chloro-3-[(CH₃)₂CHSO₂—]-4-(phenyl NHSO₂—)phenyl | —CH₂CH₂CH₂— | |
| Ia.307 | 2-(CH₃)-3(CH₃SCH₂CH₂O—)-4-CH₃NHSO₂—)-phenyl | —CH₂CH₂CH₂— | |
| Ia.308 | 2-Chloro-4-(phenyl-N=N—)phenyl | —CH₂CH₂CH₂— | |
| Ia.309 | 2-(CH₃SO₂—)-4-cyanophenyl | —CH₂CH₂CH₂— | |
| Ia.310 | 2-Bromo-4-(CH₃SO₂—)phenyl | —CH₂CH₂CH₂— | |
| Ia.311 | 2-(CH₃SO₂—)-4-bromophenyl | —CH₂CH₂CH₂— | |
| Ia.312 | 2-(CH₃)-3-(CH₃O—)-4-(NH₂SO₂—)phenyl | —CH₂CH₂CH₂— | |
| Ia.313 | 2-(CH₃)-3-(CH₃O—)-4(CH₃NHSO₂—)phenyl | —CH₂CH₂CH₂— | |
| Ia.314 | 2,3-Dichloro-4-(CH₃SO₂—)phenyl | —CH₂CH₂CH₂— | |
| Ia.315 | 2-Chloro-3-(CH₃OCH₂—)-4-(CH₃SO₂—)phenyl | —CH₂CH₂CH₂— | |
| Ia.316 | 2-Bromo-4-(phenyl-N=N—)phenyl | —CH₂CH₂CH₂— | |
| Ia.317 | 2-Chloro-3-(CH₃O—)-4-(phenyl-N=N—)-phenyl | —CH₂CH₂CH₂— | |

In addition, the 2-aroylcyclohexanediones Ib.001 to Ib.317 are particularly preferred. They differ from the corresponding compounds Ia.001 to Ia.317 in that X and Y are both sulfur:

Ib

R⁷—S\
     CH—[cyclohexenone with OH, C(=O)Ar, =O]\
R⁶—S/

(R¹–R⁵ = H)

In addition, the 2-aroylcyclohexanediones Ic.001 to Ic.317 are particularly preferred. They differ from the corresponding compounds Ia.001 to Ia.317 in that X is oxygen and Y is sulfur and R¹ is methyl:

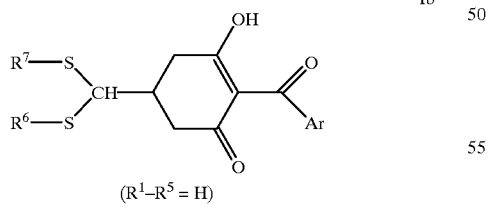

(R¹ = Methyl
R²–R⁵ = H)

The novel 2-aroylcyclohexanediones I are obtainable in various ways, for example by reaction of a cyclohexanedione of the formula II with an acid derivative of the formula III in the presence of a base (cf. eg. EP-A 186 118 and U.S. Pat. No. 4,695,673):

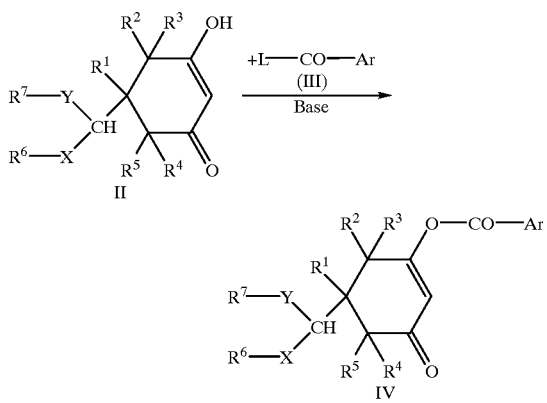

L is a nucleophilic leaving group such as chloride, bromide or cyanide.

The reaction is carried out in an inert solvent at from 0° C. to the boiling point of the particular solvent, preferably from 0 to 20° C.

Suitable solvents are, for example, chlorohydrocarbons such as methylene chloride, chloroform and dichloroethane, ethers such as tetrahydrofuran, dioxane and methyl tertiary-butyl ether, aromatic hydrocarbons such as benzene and toluene, esters such as ethyl acetate or amides such as dimethylformamide.

Suitable bases are, for example, tert-amines such as triethylamine, N-methylmorpholine and pyridine.

The base is advantageously employed in an approximately equimolar amount, based on the diketone II or the acid derivative III.

The reaction can also be carried out in a heterogeneous system, the diketone II and the base then being present in aqueous solution, to which the acid derivative is added in a water-immiscible solvent, in the presence of a phase-transfer catalyst.

Bases which can be used for this are, for example, the alkali metal and alkaline earth metal hydroxides or carbonates such as sodium hydroxide, potassium hydroxide, sodium carbonate, potassium carbonate, calcium carbonate and calcium hydroxide.

Examples of phase-transfer catalysts which can be used are ammonium, sulfonium or phosphonium salts, the nature of the anion being of secondary importance. Benzyltrimethylammonium hydroxide, for example, has proven expedient.

The enol esters of the formula IV obtained are then rearranged in the presence of a cyanide source and of a base to the desired compounds of the formula I:

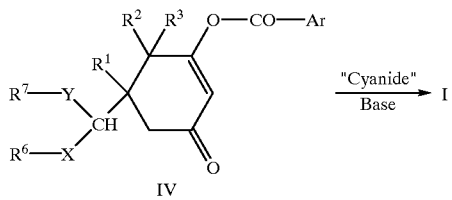

The rearrangement is customarily performed in an inert solvent at from 0° C. to the boiling point of the solvent, preferably from 20 to 40° C.

Suitable solvents are, for example, chlorohydrocarbons, such as methylene chloride, chloroform and dichloroethane, ethers such as tetrahydrofuran, dioxane and methyl tertiary-butyl ether, aromatic hydrocarbons such as benzene and toluene, nitriles such as acetonitrile, esters such as ethyl acetate, ketones such as acetone and methyl ethyl ketone or amides such as dimethylformamide.

Cyanide sources which have proven suitable are, for example, alkali metal cyanides such as sodium cyanide and potassium cyanide, cyanohydrins such as acetone cyanohydrin and trialkylsilyl cyanides such as trimethylsilyl cyanide.

Normally, a catalytic amount of cyanide, for example from 1 to 10 mol%, based on the enol ester IV, is sufficient.

Bases which can be used are, for example, trialkylamines such as triethylamine, trialkanolamines such as triethanolamine, and pyridine or inorganic bases such as alkali metal carbonates and phosphates.

It has proven advantageous to add the base in an excess of from 100 to 400 mol %, based on the enol ester IV.

The 2-aroylcyclohexanediones I can be isolated from the reaction mixtures obtained by this process by means of customary working up methods, for example by extraction or by crystallization.

Particular conditions with respect to the pressure do not have to be taken into consideration in the preparation of the compounds I; in general the reaction is therefore carried out at normal pressure or under the autogenous pressure of the particular diluent.

The diketones of the formula II have been disclosed in EP-A 233 568 or can be prepared in the manner described there.

The acid derivatives III needed are known or can be obtained by methods known per se {cf. for example The Chemistry of Carboxylic Acids and Esters, S. Patai, editor, J. Wiley and Sons, New York, N.Y.(1969); Survey of Organic Synthesis, C. A. Buehler and D. F. Pearson, J. Wiley and Sons, (1970); Reagents for Organic Synthesis, Vol. I, L. F. Fieser and M. Fieser, pp. 767–769 (1967)}.

Alkali metal salts of the compounds I can be obtained by treating I with sodium or potassium hydroxide or alkoxide in aqueous solution or in an organic solvent such as methanol, ethanol, acetone or toluene.

Other metal salts, eg. the manganese, copper, zinc, iron, calcium, magnesium and barium salts, can be prepared from the sodium salts in a customary manner, just as ammonium, phosphonium, sulfonium or sulfoxonium salts can be prepared by means of ammonia, phosphonium, sulfonium or sulfoxonium hydroxides.

The esters of the compounds I are likewise obtainable in a customary manner (cf. eg. EP-A 102 823 and EP-A 136 702).

The 2-aroylcyclohexanediones I, their salts and esters, or the compositions containing these compounds can very effectively control broad-leafed weeds and grass weeds in crops such as wheat, rice, maize, soybean and cotton without damaging the crop plants. This effect occurs especially at low application rates.

The compounds I or the herbicidal compositions containing them can be applied by spraying, atomizing, dusting, broadcasting or watering, for example in the form of directly sprayable aqueous solutions, powders, suspensions, even high-percentage aqueous, oily or other suspensions, or dispersions, emulsions, oil dispersions, pastes, dusting compositions, broadcasting compositions or granules. The application forms depend on the intended uses; in each case they should if possible ensure the finest dispersion of the active compounds according to the invention.

Suitable inert additives are mineral oil fractions of medium to high boiling point, such as kerosene or diesel oil, additionally coal tar oils and oils of vegetable or animal origin, aliphatic, cyclic and aromatic hydrocarbons, eg. paraffin, tetrahydronaphthalene, alkylated naphthalenes or their derivatives, alkylated benzenes or their derivatives, methanol, ethanol, propanol, butanol, cyclohexanol, cyclohexanone or strongly polar solvents, such as N-methylpyrrolidone or water.

Aqueous application forms can be prepared from emulsion concentrates, suspensions, pastes, wettable powders or water-dispersible granules by addition of water. To prepare emulsions, pastes or oil dispersions, the substrates as such or dissolved in an oil or solvent can be homogenized in water by means of wetting agents, adhesives, dispersants or emulsifiers. However, concentrates consisting of active substance, wetting agent, adhesive, dispersant or emulsifier and possibly solvent or oil can also be prepared, which are suitable for dilution with water.

Suitable surface-active substances are the alkali metal, alkaline earth metal and ammonium salts of aromatic sulfonic acids, eg. lignosulfonic, phenolsulfonic, naphthalenesulfonic and dibutylnaphthalenesulfonic acid, as well as of fatty acids, alkyl- and alkylarylsulfonates, alkyl, lauryl ether and fatty alcohol sulfates, and also salts of sulfated hexa-, hepta- and octadecanols and of fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ether, ethoxylated isooctyl-, octyl- or nonylphenol, alkylphenyl or tributylphenyl polyglycol ethers, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, broadcasting and dusting compositions can be prepared by mixing or joint grinding of the active substances with a solid carrier.

Granules, eg. coated, impregnated and homogeneous granules, can be prepared by binding the active compounds to solid carriers. Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products such as cereal flour, tree bark meal, wood meal and nutshell meal, cellulose powder or other solid carriers.

The formulations in general contain from 0.01 to 95% by weight, preferably from 0.5 to 90% by weight, of active compound. The active compounds are employed here in a purity of from 90% to 100%, preferably from 95% to 100% (according to NMR spectrum).

The compounds I according to the invention can furthermore be formulated, for example, as follows:

I. 20 parts by weight of the compound No. 5 are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active compound.

II. 20 parts by weight of the compound No. 9 are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

III. 20 parts by weight of the active compound No. 1 are dissolved in a mixture which consists of 25 parts by weight of cyclohexanone, 65 parts by weight of a mineral oil fraction of boiling point 210 to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IV. 20 parts by weight of the active compound No. 2 are well mixed with 3 parts by weight of the sodium salt of diisobutylnaphthalene α-sulfonic acid, 17 parts by weight of the sodium salt of a lignosulfonic acid from a sulfite waste liquor and 60 parts by weight of powdered silica gel and the mixture is ground in a hammer mill. By finely dispersing the mixture in 20,000 parts by weight of water, a spray mixture is obtained which contains 0.1% by weight of the active compound.

V. 3 parts by weight of the active compound No. 4 are mixed with 97 parts by weight of finely divided kaolin. In this way a dusting composition is obtained which contains 3% by weight of the active compound.

VI. 20 parts by weight of the active compound No. 7 are intimately mixed with 2 parts by weight of calcium salt of dodecylbenzenesulfonic acid, 8 parts by weight of fatty alcohol polyglycol ether, 2 parts by weight of sodium salt of a phenol/urea/formaldehyde condensate and 68 parts by weight of a paraffinic mineral oil. A stable oily dispersion is obtained.

The application of the herbicidal compositions or of the active compounds can be carried out pre-emergence or post-emergence. If the active compounds are less tolerable for certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

Depending on the target of control, time of year, target plants and stage of growth, the application rates of active compound are from 0.001 to 3.0, preferably from 0.01 to 2.0, kg/ha of active substance (a.s.).

In consideration of the variety of application methods, the compounds I or compositions containing them can additionally be employed in a further number of crop plants for the elimination of undesired plants. Suitable crops are, for example, the following:

*Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cyn-*

*odon dactylon, Daucus carota, Elaeis guineensis, Fragaria vesca, Glycine max, Gossypium hirsutum* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spp., *Manihot esculenta, Medicago sativa,* Musa spp., *Nicotiana tabacum* (*N. rustica*), *Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera, Zea mays.*

Moreover, the compounds I can be employed in crops which tolerate the action of herbicides as a result of breeding, including genetic engineering methods.

The compounds of the formula I can furthermore affect the various 30 stages of development of a plant and are therefore employed as growth regulators. The varied action of the plant growth regulators is especially dependent a) on the plant species and variety, b) on the time of application, relative to the stage of development of the plant, and on the time of year, c) on the site of application and application process (eg. seed dressing, soil treatment, foliar application or stem injection in the case of trees), d) on climatic factors (eg. temperature, amount of precipitation, additionally length of day and light intensity), e) on the soil condition (including fertilization), f) on the formulation and application form of the active compound and g) on the concentrations of the active substance used.

A few of the number of different possibilities for application of the plant growth regulators of the formula I according to the invention in plant cultivation, in agriculture and in horticulture are mentioned below:

A.

The vegetative growth of the plants can be severely inhibited by the compounds which can be used according to the invention, which is manifested in particular in a reduction in the longitudinal growth. The treated plants accordingly exhibit stocky growth; additionally darker leaf coloration is to be observed.

A decreased intensity in the growth of grasses on roadsides, hedgerows, canal banks and on plots of grass such as parks, sports grounds and orchards, ornamental lawns and airfields proves to be advantageous in practice, so that the labor- and cost-intensive mowing can be reduced.

The increase in the resistance of crops susceptible to lodging, such as cereals, maize, sunflowers and soybeans, is also of economic interest. The culm shortening and culm strengthening caused in this case decrease or eliminate the danger of lodging (of being bent over) of plants under unfavorable weather conditions before harvesting.

The application of growth regulators for inhibiting the longitudinal growth and for temporally altering the course of ripening in cotton is also important. Completely mechanized harvesting of this important crop plant is thus made possible.

In the case of fruit and other trees, pruning costs can be saved using the growth regulators. In addition, the alternation of fruit trees can be broken by means of growth regulators.

The lateral branching of the plants can also be increased or inhibited by application of growth regulators. There is interest in this if, eg. in the case of tobacco plants, the formation of side shoots (suckers) is to be inhibited in favor of leaf growth.

In the case of winter rape, for example, the frost resistance can also be considerably increased using growth regulators. In this case, on the one hand, the longitudinal growth and the development of an excessively luxuriant (and thereby particularly frost-susceptible) herbage or biomass are inhibited. On the other hand, after sowing and before the winter frosts set in the young rape plants are held back in the vegetative development stage despite favorable growth conditions. As a result, the frost danger to those plants which are prone to premature degeneration of the inhibition of flowering and to transition into the generative phase is also eliminated. Even in other crops, eg. winter cereals, it is advantageous if the populations are indeed well tillered by treatment with compounds according to the invention in the fall, but are not too luxuriant when going into the winter. As a result, the increased frost sensitivity and, because of the relatively low herbage or biomass, attack by various diseases (eg. fungal disease) can be prevented. The inhibition of the vegetative growth additionally makes possible a more compact planting of the soil with many crop plants, so that an additional yield can be achieved, based on the soil area.

B.

Additional yields both of parts of plants and of plant constituents can be achieved using the growth regulators. Thus it is possible, for example, to induce the growth of greater amounts of buds, flowers, leaves, fruit, seeds, roots and tubers, to increase the content of sugar in sugar beet, sugar cane and citrus fruits, to raise the protein content in cereals or soybeans or to stimulate rubber trees to an increased flow of latex.

In this case, the compounds of the formula I can cause increases in yield by intervention in the plant metabolism or by promotion or inhibition of vegetative and/or of generative growth.

C.

Finally, both reduction or prolongation of the development stages and acceleration or retardation of the ripening of the harvested parts of plants before or after harvesting can be achieved using plant growth regulators.

Of economic interest, for example, is the facilitation of harvesting, which is made possible by the temporally concentrated fall or decrease in the adhesiveness to the tree in the case of citrus fruits, olives or in the case of other species and varieties of pomes, drupes and indehiscent fruit. The same mechanism, that is the promotion of the formation of abscission tissue between the fruit or leaf and shoot part of the plant, is also essential for a well-controllable defoliation of productive plants such as, for example, cotton.

D.

The consumption of water by plants can furthermore be reduced using growth regulators. This is particularly important for usable agricultural areas which have to be artificially watered with a high outlay in terms of cost, eg. in arid or semiarid areas. By the use of the substances according to the invention, the intensity of watering can be reduced and thus a more cost-effective management can be carried out. Under the influence of growth regulators, a better utilization of the water present occurs because, inter alia, the opening width of the stomata is reduced, a thicker epidermis and cuticle are formed, the root penetration of the soil is improved and the microclimate in the plant population is favorably influenced by a more compact growth.

The compounds I are particularly suitable for culm shortening of crop plants such as barley, rape and wheat.

The growth regulators of the formula I to be used according to the invention can be supplied to the crop plants both from seeds (as seed-dressing agents) and via the soil, ie. by the roots and, particularly preferably, by spraying over the leaf. The compositions are prepared here in a similar manner to the herbicides (see above).

As a result of the high plant compatibility, the application rate of active compound is not critical. The optimum application rate varies depending on the target of control, time of year, target plants and stages of growth.

To widen the spectrum of action and to achieve synergistic effects, the 2-aroylcyclohexanediones I can be mixed with numerous representatives of other herbicidal or growth-regulating active compound groups and applied together. For example, suitable herbicidal mixture components are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry eg. a carboxyl or carbimino group in the 2-position, quinolinecarboxylic acid derivatives, imidazolinones, sulfonamides, sulfonylureas, aryloxy- and heteroaryloxyphenoxypropionic acids and their salts, esters and amides and others. Suitable growth regulators are in particular chlormequat chloride, ethephon and mepiquat chloride.

It may additionally be useful to apply the compounds I on their own or together in combination with other herbicides or growth regulators and additionally mixed with further crop protection agents, for example with agents for controlling pests or phytopathogenic fungi or bacteria. Additionally of interest is the miscibility with mineral salt solutions which are employed for the elimination of nutritional and trace element deficiencies. Nonphytotoxic oils and oil concentrates can also be added.

PREPARATION EXAMPLE 2-(2-Chloro-4-methylsulfonylbenzoyl)-5-dimethoxymethyl-1,3-cyclohexanedione

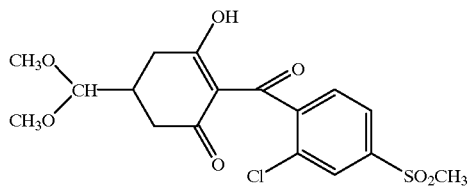

A solution of 1.7 g (4.2 mmol) of 5-dimethoxymethyl-3-oxo-1-cyclohexen-1-yl 2-chloro-4-methylsulfonylbenzoate and 0.2 g (2.3 mmol) of acetone cyanohydrin in 70 ml of acetonitrile was stirred at about 20° C. with 2.2 g (22 mmol) of triethylamine in 10 ml of acetonitrile and treated dropwise with 30 ml of a 3% strength aqueous hydrochloric acid solution. The reaction mixture was then extracted with methyl tert-butyl ether and the extracts were washed four times with 5% strength aqueous potassium carbonate solution. The combined aqueous phases were acidified with hydrochloric acid at 10–20° C. and then extracted twice with methyl tert-butyl ether. The combined ether phases were dried, filtered and then purified by chromatography on silica gel. Yield: 41%.

Intermediate:

5-Dimethoxymethyl-3-oxo-1-cyclohexen-1-yl 2-chloro-4-methylsulfonylbenzoate

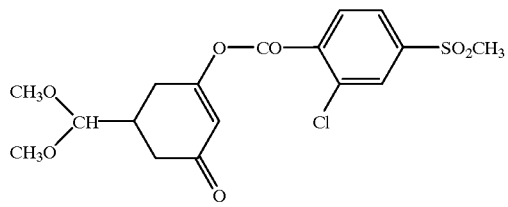

1.4 g (5.4 mmol) of 2-chloro-4-methylsulfonylbenzyl chloride in 10 ml of tetrahydrofuran were added dropwise at 0° C. to a mixture of 1.0 g (5.4 mmol) of 5-dimethoxymethyl-1,3-cyclohexanedione, 0.54 g (5.4 mmol) of triethylamine and 20 ml of tetrahydrofuran. The mixture was then stirred for one hour at 0° C. and a further 2 hours at about 20° C., after which 80 ml of methyl chloride were added to the reaction mixture. The organic phase was washed once with water, once with half-concentrated aqueous sodium carbonate solution and then a further two times with water. After this purification the organic phase was dried, filtered and finally concentrated. Yield: 79%.

The following Tables 2 and 3 show further 2-aroylcyclohexanediones I which were prepared or can be prepared in the same manner:

TABLE 2

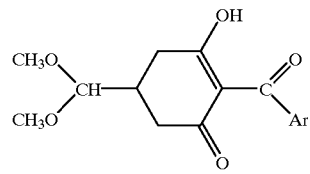

$(R^1–R^5 = H; X, Y = O; R^6, R^7 = CH_3)$

| No. | Ar | physical data ($^1$H-NMR, in CDCl$_3$: δ[ppm]) |
|---|---|---|
| Id.01 | 2-Nitro-4-(CH$_3$—SO$_2$—)phenyl | 8.67(d, 1H); 8.24(dd, 1H); 7.45(d, 1H); 4.20(d, 1H); 3.41(s, 3H); 3.39(s, 3H); 3.16(s, 3H); 2.82(m, 2H); 2.43(m, 2H); 2.30(m, 1H) |
| Id.02 | 2-Nitro-4-chlorophenyl | 8.20(d, 1H); 7.64(dd, 1H); 7.18(d, 1H); 4.17(d, 1H); 3.40(s, 3H); 3.38(s, 3H); 2.75(m, 2H); 2.42(m, 2H); 2.28(m, 1H) |
| Id.03 | 2-Chloro-4-nitrophenyl | 8.28(d, 1H); 8.19(dd, 1H); 7.37(d, 1H); 4.23(d, 1H); 3.41(s, 3H); 3.39(s, 3H); 2.83(m, 2H); 2.48(m, 2H); 2.33(m, 1H) |
| Id.04 | 2-(CH$_3$—SO$_2$—)-4-fluorophenyl | 7.70(m, 1H); 7.33(m, 1H); 7.20(m, 1H); 4.21(d, 1H); 3.41(s, 3H); 3.39(s, 3H); 3.15(s, 3H); 2.78(m, 2H); 2.45(m, 2H); 2.32(m, 1H) |
| Id.05 | 2-Chloro-(4-CH$_3$—SO$_2$—)phenyl | 7.96(d, 1H); 7.90(dd, 1H); 7.38(d, 1H); 4.22(d, 1H); 3.42(s, 3H); 3.40(s, 3H); 3.12(s, 3H); 2.83(m, 2H); 2.50(m, 2H); 2.41(m, 1H) |
| Id.06 | 4-(Phenyl-N=N—)phenyl | 7.92(m, 4H); 7.67(d, 2H); 7.52(m, 3H); 4.23(d, 1H); 3.44(s, 6H); 2.73(m, 2H); 2.61(m, 2H); 2.42(m, 1H) |
| Id.07 | 2,4-Dichlorophenyl | 7.39(d, 1H); 7.36(dd, 1H); 7.17(d, 1H); 4.20(d, 1H); |

TABLE 2-continued

Id (R¹–R⁵ = H; X, Y = O; R⁶, R⁷ = CH₃)

| No. | Ar | physical data (¹H-NMR, in CDCl₃: δ[ppm]) |
|---|---|---|
| Id.08 | 2-(CH₃—SO₂—)-4-nitrophenyl | 3.39(s, 3H); 3.37(s, 3H); 2.78(m, 2H); 2.50(m, 2H); 2.35(m, 1H) 8.83(d, 1H); 8.49(dd, 1H); 7.38(d, 1H); 4.20(d, 1H); 3.42(s, 3H); 3.40(s, 3H); 3.18(s, 3H); 2.82(m, 2H); 2.50(m, 2H); 2.34(m, 2H) |
| Id.09 | 2-Chloro-3-ethoxy-4-(C₂H₅—SO₂—)-phenyl | 7.91(d, 1H); 7.08(d, 1H); 4.30(q, 2H); 4.22(d, 1H); 3.45(q, 2H); 3.42(s, 3H); 3.40(s, 3H); 2.82(m, 2H); 2.50(m, 2H); 2.36(m, 1H); 1.49(t, 3H); 1.27(t, 3H) |
| Id.10 | 2-Methyl-3-methoxy-4-(CH₃—SO₂-)-phenyl | 7.81(d, 1H); 6.93(d, 1H); 4.21(d, 1H); 3.93(s, 3H); 3.42(s, 6H); 3.23(s, 1H); 2.83(m, 2H); 2.50(m, 3H); 2.22(s, 3H) |

TABLE 2-continued

Id (R¹–R⁵ = H; X, Y = O; R⁶, R⁷ = CH₃)

| No. | Ar | physical data (¹H-NMR, in CDCl₃: δ[ppm]) |
|---|---|---|
| Id.11 | 2-Chloro-3-methoxy-4-(CH₃—SO₂)-phenyl | 7.93(d, 1H); 7.08(d, 1H); 4.21(d, 1H); 4.1(s, 3H); 3.41(s, 3H); 3.40(s, 3H); 3.27(s, 3H); 2.85(m, 2H); 2.5(m, 2H); 2.32(m, 1H) |
| Id.12 | 2-(CH₃—SO₂-)-4-chlorophenyl | |
| Id.13 | 2-Chloro-5-(CH₃—SO₂—)phenyl | |
| Id.14 | 2-Chloro-3-methyl-4-(methyl-sulfonyl)phenyl | 7.92(d, 1H); 7.08(d, 1H); 4.2(d, 1H) |
| Id.15 | 2-Chloro-3-chloro-4-methoxy-phenyl | 7.13(d, 1H); 6.9(d, 1H); 4.2(d, 1H); 3.96(s, 3H); 3.42(s, 3H); 3.40(s, 3H); 2.8(m, 2H); 2.5(m, 2H); 2.32(m, 1H) |
| Id.16 | 2-Chloro-3-chloro-4-(methyl-sulfonyl)phenyl | 8.14(d, 1H); 7.24(d, 1H); 4.21(d, 1H); 3.41(s, 6H); 3.3(s, 3H); 2.83(m, 2H); 2.49(m, 2H); 2.3(m, 1H) |

TABLE 3

Ie (R¹–R⁵ = H)

| No. | X, Y | R⁶ | R⁷ | Ar | physical data |
|---|---|---|---|---|---|
| Ie.001 | O | —CH₂—CH₂— | | 2-Nitro-4-chlorophenyl | |
| Ie.002 | O | —CH₂—CH₂— | | 2-Chloro-3-ethoxy-4-(C₂H₅—SO₂—)phenyl | |
| Ie.003 | O | —CH₂—CH₂— | | 2-Methyl-3-methoxy-4-(CH₃—SO₂—)phenyl | |
| Ie.004 | O | —CH₂—CH₂— | | 2-Chloro-3-methoxy-4-(CH₃SO₂—)phenyl | |
| Ie.005 | O | —CH₂—CH₂— | | 2-Chloro-5-(CH₃—SO₂—)phenyl | |
| Ie.006 | O | —CH₂—C(CH₃)₂—CH₂— | | 2-Nitro-4-chlorophenyl | 8.17(d, 1H); 7.65(dd, 1H); 7.18(d, 1H); 4.38(d, 1H); 3.62(d, 2H); 3.4(d, 2H); 2.79(m, 2H); 2.42(s, br., 3H); 1.14(s, 3H); 0.74(s, 3H) |
| Ie.007 | O | —CH₂—C(CH₃)₂—CH₂— | | 2-Chloro-3-ethoxy-4-(C₂H₅—SO₂—)phenyl | 7.92(d, 1H); 7.07(d, 1H); |

TABLE 3-continued

Ie (R¹–R⁵ = H)

| No. | X, Y | R⁶ | R⁷ | Ar | physical data |
|---|---|---|---|---|---|
| | | | | | 4.4(d, 1H); 4.29(q, 2H); 3.62(d, 2H); 3.45(q, 2H); 3.4(d, 2H); 2.92(m, 2H); 2.5(m, 3H); 1.4(t, 3H); 1.26(t, 3H); 1.18(s, 3H); 0.74(s, 3H) |
| Ie.008 | O | —CH₂—C(CH₃)₂—CH₂— | | 2-Methyl-3-methoxy-4-(CH₃—SO₂—)phenyl | 7.83(d, 1H); 6.97(d, 1H); 4.41(d, 1H); 3.95(s, 3H); 3.62(d, 2H); 3.43(d, 2H); 3.28(s, 3H); 2.91(m, 2H); 2.49(m, 3H); 2.2(s, 3H); 1.16(s, 3H); 0.73(s, 3H) |
| Ie.009 | O | —CH₂—C(CH₃)₂—CH₂— | | 2-Chloro-3-methoxy-4-(CH₃—SO₂—)phenyl | 7.93(d, 1H); 7.08(d, 1H); 4.4(d, 1H); 4.08(s, 3H); 3.61(d, 2H); 3.42(d, 2H); 3.25(s, 3H); 2.91(m, 2H); 2.5(m, 3H); 1.16(s, 3H); 0.73(s, 3H) |
| Ie.010 | O | —CH₂—C(CH₃)₂—CH₂— | | 2-Chloro-5-(CH₃—SO₂—)phenyl | |
| Ie.011 | O | C₂H₅ | C₂H₅ | 2-Nitro-4-chlorophenyl | |
| Ie.012 | O | C₂H₅ | C₂H₅ | 2-Chloro-3-ethoxy-4-(C₂H₅—SO₂—)phenyl | |
| Ie.013 | O | C₂H₅ | C₂H₅ | 2-Methyl-3-methoxy-4-(CH₃—SO₂—)phenyl | |
| Ie.014 | O | C₂H₅ | C₂H₅ | 2-Chloro-3-methoxy-4-(CH₃—SO₂—)phenyl | |
| Ie.015 | O | C₂H₅ | C₂H₅ | 2-Chloro-3-(CH₃—SO₂—)phenyl | |
| Ie.016 | S | CH₃ | CH₃ | 2-Nitro-4-chlorophenyl | |
| Ie.017 | S | CH₃ | CH₃ | 2-Chloro-3-ethoxy-4-(C₂H₅—SO₂—)phenyl | |
| Ie.018 | S | CH₃ | CH₃ | 2-Methyl-3-methoxy-4-(CH₃—SO₂—)phenyl | |
| Ie.019 | S | CH₃ | CH₃ | 2-Chloro-3-methoxy-4-(CH₃—SO₂—)phenyl | |
| Ie.020 | S | CH₃ | CH₃ | 2-Chloro-5-(CH₃—SO₂—)phenyl | |
| Ie.021 | S | C₂H₅ | C₂H₅ | 2-Nitro-4-chlorophenyl | |
| Ie.022 | S | C₂H₅ | C₂H₅ | 2-Chloro-3-ethoxy-4-(C₂H₅—SO₂—)phenyl | |
| Ie.023 | S | C₂H₅ | C₂H₅ | 2-Methyl-3-methoxy-4-(CH₃—SO₂—)phenyl | |
| Ie.024 | S | C₂H₅ | C₂H₅ | 2-Chloro-3-methoxy-4-(CH₃—SO₂—)phenyl | |
| Ie.025 | S | C₂H₅ | C₂H₅ | 2-Chloro-5-(CH₃—SO₂—)phenyl | |
| Ie.026 | S | —CH₂—CH₂— | | 2-Nitro-4-chlorophenyl | |
| Ie.027 | S | —CH₂—CH₂— | | 2-Chloro-3-ethoxy-4-(C₂H₅—SO₂—)phenyl | |
| Ie.028 | S | —CH₂—CH₂— | | 2-Methyl-3-methoxy-4-(CH₃—SO₂—)phenyl | |
| Ie.029 | S | —CH₂—CH₂— | | 2-Chloro-3-methoxy-4-(CH₃—SO₂—)phenyl | |
| Ie.030 | S | —CH₂—CH₂— | | 2-Chloro-5-(CH₃—SO₂—)phenyl | |
| Ie.031 | S | —CH₂—CH₂—CH₂— | | 2-Nitro-4-chlorophenyl | 8.16(d, 1H); 7.67(dd, 1H); 7.18(d, 1H); 4.09(d, 1H); 3.0(m, 2H); 2.84(m, 4H); 2.5(m, 3H); 2.1(m, 1H); 1.78(m, 1H) |
| Ie.032 | S | —CH₂—CH₂—CH₂— | | 2-Chloro-3-ethoxy-4-(ethylsulfonyl)phenyl | 7.92(d, 1H); 7.08(d, 1H); 4.3(q, 2H); 4.12(d, 1H); 3.47(q, 2H0; 3.10(m, 2H); 2.9(m, 4H); 2.5(m, 3H); 2.14(m, 1H); 1.9(m, 1H); 1.48(t, 3H); 1.27(t, 3H) |
| Ie.033 | S | —CH₂—CH₂—CH₂— | | 2-Methyl-3-methoxy-4-(methylsulfonyl)-phenyl | |
| Ie.034 | S | —CH₂—CH₂—CH₂— | | 2-Chloro-3-methoxy-4-(methylsulfonyl)-phenyl | 7.93(d, 1H); 7.06(d, 1H); 4.16(d, 1H); 4.06(s, 3H); 3.24(s, 3H); 3.0(m, 2H); 2.92(m, 4H); 2.5(m, 3H); 2.1(m, 1H); 1.9(m, 1H) |
| Ie.035 | S | —CH₂—CH₂—CH₂13 | | 2-Chloro-5-(methylsulfonyl)phenyl | |

TABLE 4

Ic (structure shown: cyclohexanedione with OH, C(=O)Ar, R⁸-X-CH(R⁷-Y)- substituents; R¹ = Methyl, R²–R⁵ = H)

| No. | X | Y | R⁶, R⁷ | Ar |
|---|---|---|---|---|
| Ic.120 | O | S | —CH₂—CH₂— | 2-Chloro-3-methoxy-4-(methylsulfonyl)phenyl |
| Ic.121 | O | S | —CH₂—CH₂— | 2-Methyl-3-methoxy-4-(methylsulfonyl)phenyl |
| Ic.122 | O | S | —CH₂—CH₂— | 2-Chloro-3-ethoxy-4-(ethylsulfonyl)-phenyl |
| Ic.137 | O | S | —CH₂—CH₂— | 2-Nitro-4-chlorophenyl |

USE EXAMPLES

It was possible to show the herbicidal and growth-regulatory action of the 2-aroylcyclohexanediones of the formula I by greenhouse tests:

The cultivation containers used were plastic flowerpots containing loamy sand with about 3.0% humus as a substrate. The seeds of the test plants were sown separately according to species.

In the case of pre-emergence treatment, the active compounds suspended or emulsified in water were applied directly after sowing by means of finely dispersing nozzles. The containers were lightly watered in order to promote germination and growth and then covered with transparent plastic hoods until the plants had taken root. This covering causes a uniform germination of the test plants if this has not been adversely affected by the active compounds.

For the purpose of post-emergence treatment, the test plants, depending on growth form, were first raised to a growth height of from 3 to 15 cm and only then treated with the active compounds suspended or emulsified in water. To do this, the test plants were either sown directly and raised in the same containers or they were first raised separately as seed plants and transplanted into the test containers a few days before the treatment. The application rate for post-emergence treatment is 0.25 or 0.125 kg/ha of a.s.

The plants were kept in a species-specific manner at 10–25° C. or 20–35° C. The test period extended over 2 to 4 weeks. During this time the plants were tended, and their reaction to the individual treatments was assessed.

The herbicidal action was assessed on a scale of from 0 to 100. 100 here means no emergence of the plants or complete destruction at least of the above-ground parts and 0 means no damage or normal course of growth.

The growth-regulating action was determined by height measurement. At the end of the test, the growth heights of the treated plants were measured and related to the growth heights of untreated plants.

The plants used in the greenhouse tests were made up of the following species:

| Botanical name | Common name |
|---|---|
| *Chenopodium album* | lamb's quarters (goosefoot) |
| *Echinochloa crus-galli* | barnyard grass |
| *Setaria viridis* | green foxtail |
| *Solanum nigrum* | black nightshade |
| *Triticum aestivum* | winter wheat |
| *Veronica spp.* | speedwell |
| *Zea mays* | Indian corn |

The results showed that undesired plants can be very well controlled using compound Nos. 05 and 09.

We claim:

1. A 2-aroylcyclohexanedione of the formula I

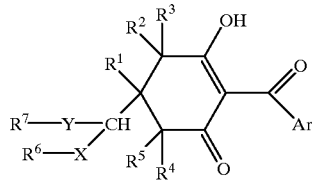

(I)

where the variables have the following meanings:

$R^1$ is hydrogen;

$R^2$, $R^3$ and $R^4$ independently of one another are hydrogen or $C_1$–$C_4$-alkyl;

$R^5$ is hydrogen, $C_1$–$C_4$-alkyl or ($C_1$–$C_4$-alkoxy)carbonyl;

$R^6$ and $R^7$ independently of one another are $C_1$–$C_4$-alkyl, benzyl or together are an ethylene or propylene chain, where each methylene unit may carry one or two $C_1$–$C_4$-alkyl radicals;

X and Y are oxygen;

Ar is phenyl, which carries from one to four substituents selected from the group consisting of halogen cyano, nitro, —N=N—Ph, ($C_1$–$C_4$-alkoxy)carbonyl, —N($R^9$)—COR$^{10}$, —N($R^9$)—SO$_2$—R$^{11}$, —SO$_2$—N($R^9$)R$^{10}$, —S(O)$_m$—R$^8$, $C_1$–$C_4$-alkyl, $C_1$–$C_4$-alkoxy, $C_1$–$C_4$-haloalkyl and $C_1$–$C_4$-haloalkoxy, where the four last-mentioned radicals in turn may carry one or two of the following substituents: $C_1$–$C_4$-alkoxy, $C_1$–$C_4$-alkylthio and/or cyano;

Ph is phenyl which may carry one to three substituents selected from the group consisting of halogen, cyano, nitro, —S(O)$_n$—R$^{23}$, ($C_1$–$C_4$-alkoxy)carbonyl, —SO$_2$—N($R^{24}$)R$^{25}$, —N($R^{24}$)—COR$^{25}$, —N($R^{24}$)—SO$_2$R$^{26}$, $C_1$–$C_4$-alkyl, $C_1$–$C_4$-alkoxy, $C_1$–$C_4$-haloalkyl and $C_1$–$C_4$-haloalkoxy, where the four last-mentioned radicals in turn may carry one or two of the following substituents: $C_1$–$C_4$-alkoxy, $C_1$–$C_4$-alkylthio and/or cyano;

m and n independently of one another are 0, 1 or 2;

$R^8$ and $R^{23}$ independently of one another are $C_1$–$C_4$-alkyl or $C_1$–$C_4$-haloalkyl, which both may carry one or two $C_1$–$C_4$-alkoxy, $C_1$–$C_4$-alkylthio and/or cyano radicals;

$R^9$, $R^{10}$, $R^{24}$ and $R^{25}$ independently of one another are hydrogen, $C_1$–$C_4$-alkyl, $C_1$–$C_4$-haloalkyl or phenyl, which may carry one to three halogen, $C_1$–$C_4$-alkyl, and/or $C_1$–$C_4$-alkoxy radicals;

$R^{11}$ and $R^{26}$ independently of one another are $C_1$–$C_4$-alkyl or $C_1$–$C_4$-haloalkyl, both may carry one or two cyano, phenyl and/or benzyl radicals;

or an agriculturally utilizable salt of I or an ester of I with a $C_1$–$C_{10}$-carboxylic, sulfonic or phosphonic acid or inorganic acid.

2. The 2-aroylcyclohexanedione of the formula I as defined in claim 1, where one substituent of Ar is selected from the group consisting of —N=N—Ph, $S(O)_m$—$R^8$, ($C_1$–$C_4$-alkoxy)carbonyl, —N($R^9$)—$SO_2$—$R^{11}$, —$SO_2$—N($R^9$)$R^{10}$, —N($R^9$)—$COR^{10}$ or $C_1$–$C_4$-haloalkyl.

3. A process for preparing a 2-aroylcyclohexanedione of the formula I as defined in claim 1, which comprises reacting a compound of the formula II

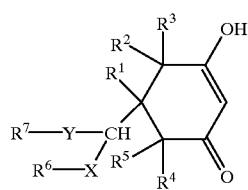

(II)

with an acid chloride of the formula III

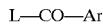

(III)

where L is a leaving group, in an inert solvent in the presence of a base, and rearranging the enol ester, obtained in this process, of the formula IV

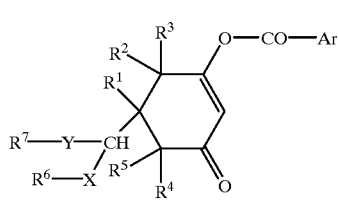

(IV)

in an inert solvent in the presence of a cyanide source and a base.

4. A herbicidal composition, containing a herbicidally active amount of a 2-aroylcyclohexanedione of the formula I or an agriculturally utilizable salt or an ester of I, as defined in claim 1, and an inert liquid or solid carrier and optionally an adjuvant.

5. A composition for regulating plant growth, containing an active amount of a 2-aroylcyclohexanedione of the formula I or an agriculturally utilizable salt or an ester of I, as defined in claim 1, and an inert liquid or solid carrier and optionally an adjuvant.

6. A process for preparing a herbicidally active composition or a composition for regulating plant growth, which comprises mixing an active amount of a 2-aroylcyclohexanedione of the formula I or an agriculturally utilizable salt or an ester of I, as defined in claim 1, and an inert liquid or solid carrier and optionally an adjuvant.

7. A method of controlling undesired plant growth, which comprises allowing a herbicidally active amount of a 2-aroylcyclohexanedione of the formula I or an agriculturally utilizable salt or an ester of I, as defined in claim 1, to act on plants, their habitat or on seed.

8. A method of regulating undesired plant growth, which comprises allowing an amount of a 2-aroylcyclohexanedione of the formula I effective for regulating plant growth, or of an agriculturally utilizable salt or an ester of I, as defined in claim 1, to act on plants, their habitat or seed.

9. The 2-aroylcyclohexanedione of the formula I as defined in claim 1, wherein $R^2$, $R^3$ and $R^4$ are hydrogen.

10. The 2-aroylcyclohexanedione of the formula I as defined in claim 1, wherein $R^6$ and $R^7$ together are an ethylene or propylene chain, where each methylene unit may carry one or two $C_1$–$C_4$-alkyl radicals.

11. The 2-aroylcyclohexanedione of the formula I as defined in claim 1 wherein $R^6$ is $C_1$–$C_4$-alkyl or benzyl.

12. The 2-aroylcyclohexanedione of the formula I as defined in claim 1 wherein $R^7$ is $C_1$–$C_4$-alkyl or benzyl.

* * * * *

UNITED STATES PATENT AND TRADEMARK OFFICE
CERTIFICATE OF CORRECTION

PATENT NO. : 6,040,274
DATED : March 21, 2000
INVENTOR(S) : KAST et al.

It is certified that error appears in the above-identified patent and that said Letters Patent is hereby corrected as shown below:

IN THE CLAIMS

Column 38, claim 8, line 29, before "seed" insert -- or--.

Signed and Sealed this

Twenty-seventh Day of February, 2001

Attest:

NICHOLAS P. GODICI

Attesting Officer     Acting Director of the United States Patent and Trademark Office